US006960586B2

(12) United States Patent
Tasaka et al.

(10) Patent No.: US 6,960,586 B2
(45) Date of Patent: Nov. 1, 2005

(54) IMIDAZOLE DERIVATIVES, PROCESS FOR THEIR PREPARATION AND THEIR USE

(75) Inventors: Akihiro Tasaka, Osaka (JP); Nobuyuki Matsunaga, Osaka (JP); Akio Ojida, Fukuoka (JP); Masami Kusaka, Hyogo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 117 days.

(21) Appl. No.: 10/416,998

(22) PCT Filed: Nov. 19, 2001

(86) PCT No.: PCT/JP01/10079

§ 371 (c)(1),
(2), (4) Date: May 16, 2003

(87) PCT Pub. No.: WO02/40470

PCT Pub. Date: May 23, 2002

(65) Prior Publication Data

US 2004/0024039 A1 Feb. 5, 2004

(30) Foreign Application Priority Data

Nov. 20, 2000 (JP) ........................................ 2000-353634
Dec. 15, 2000 (JP) ........................................ 2000-382056

(51) Int. Cl.$^7$ .................... A01N 43/58; A01N 43/60; A01N 43/42; A61K 31/495; A61K 31/50
(52) U.S. Cl. .................... 514/248; 514/290; 514/387; 514/397; 544/234; 546/101; 548/302.1; 548/311.4; 548/311.7; 548/399
(58) Field of Search ................... 514/248, 290, 514/387, 397; 544/234; 546/101; 548/302.1, 311.4, 311.7, 399

(56) References Cited

U.S. PATENT DOCUMENTS 5,491,161 A  2/1996  Janssen et al. .............. 514/394

FOREIGN PATENT DOCUMENTS

| EP | 0260744 | 3/1988 |
|----|---------|--------|
| EP | 0288053 | 10/1988 |
| EP | 0413270 | 2/1991 |
| EP | 0721943 | 7/1996 |
| EP | 0974584 | 1/2000 |
| EP | 1028110 | 8/2000 |
| WO | WO 92/15404 | 9/1992 |
| WO | WO 92/15604 | 9/1992 |
| WO | WO 94/27989 | 12/1994 |
| WO | WO 96/14090 | 5/1996 |
| WO | WO 97/00257 | 1/1997 |
| WO | WO 93/20097 | 10/1998 |
| WO | WO 99/54309 | 10/1999 |

OTHER PUBLICATIONS

Njar and Brodie, "Inhibitors of 17alpha–Hydroxylase/17, 20–Lyase (CYP17): Potential Agents for the Treatment of Prostate Cancer" Current Pharmaceutical Design, vol. 5, pp. 163–180 (1990).*

Beckmann et al. "Multistep carcinogenesis of breast cancer and tumour heterogeneity" Journal of Molecular Medicine, vol. 75(6 pp. 429–439 (1997).*

Al–Dabbagh and Smith, "Species differences in oxidative drug metabolism: some basic considerations." Archives of toxicology. Supplement. Archiv fur Toxikologie. supplement, vol. 7, pp. 219–231 (1984).*

Hans Bundgaard, Design of Prodrugs, p. 1. © 1985 Elsevier Science Publishers.*

Richard B. Silverman, The Organic Chemistry of Drug Design and Drug Action, pp. 352–400. © 1992 Academic Press, Inc.*

Ingvarsson, "Molecular genetics of breast cancer progression" Seminars in Cancer Biology, vol. 9, pp. 277–288 (1999).*

Wachall, et al. "Imidazole Substituted Biphenyls: A New Class of Highly Potent and In Vivo Active Inhibitors of P450 17 as Potential Therapeutics for Treatment of Prostate Cancer" Bioorganic & Medicinal Chemistry 7:1913–1924 (1999).

Zhuang, et al. "Novel Imidazolyl and Triazolyl Substituted Biphenyl Compounds: Synthesis and Evaluation as Nonsteroidal Inhibitors of Human 17 α–Hydroxylase–C17, 20–Lyase (P450 17)" Bioorganic & Medicinal Chemistry 8: 1245–1252 (2000).

* cited by examiner

Primary Examiner—James O. Wilson
Assistant Examiner—Zachary C. Tucker
(74) Attorney, Agent, or Firm—Elaine M. Ramesh; Mark Chao

(57) ABSTRACT

The present invention provides a compound having a steroid $C_{17,20}$-lyase inhibitory activity, which is useful as a prophylactic or therapeutic agent of prostatism and tumor such as breast cancer and the like.

A compound represented by the formula:

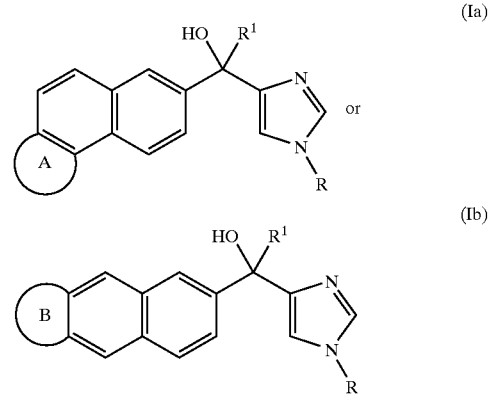

wherein R is a hydrogen atom or a protecting group, $R^1$ is a lower alkyl group or a cyclic alkyl group, and ring A and ring B are each an optionally substituted 5-membered or 6-membered ring having an amide bond in the ring, or a salt thereof.

10 Claims, No Drawings

IMIDAZOLE DERIVATIVES, PROCESS FOR THEIR PREPARATION AND THEIR USE

This application is the National Phase filing of International Patent Application No. PCT/JP01/10079, filed 19 Nov. 2001.

TECHNICAL FIELD OF THE INVENTION

The present invention relates to a pharmaceutical agent, particularly, a novel imidazole derivative having a steroid $C_{17,20}$-lyase inhibitory action, a salt thereof and a pharmaceutical composition containing the same.

BACKGROUND OF THE INVENTION

Androgen and estrogen, which are sex hormones, have various physiological activities such as differentiation and proliferation of cells and the like. On the other hand, it has been found that androgen and estrogen act as an exacerbation factor in some diseases. It is known that steroid $C_{17,20}$-lyase is involved in the final stage in the biosynthesis of androgen in vivo. That is, steroid $C_{17,20}$-lyase converts, as a substrate, 17-hydroxypregnenolone and 17-hydroxyprogesterone derived from cholesterol to dehydroepiandrosterone and androstenedione, respectively. Therefore, a medicine having a steroid $C_{17,20}$-lyase inhibitory activity suppresses formation of androgen, as well as estrogen produced from androgen as a substrate, and is useful as an agent for the prophylaxis or treatment of diseases whose exacerbation factor is androgen or estrogen. As the disease for which androgen or estrogen is an exacerbation factor, there are mentioned, for example, prostate cancer, prostatic hypertrophy, virilism, hirsutism, male pattern alopecia, precocious puberty, breast cancer, uterine cancer, ovarian cancer, mastopathy, uterus myoma, endometriosis, adenomyosis of uterus, polycystic ovary syndrome, and the like.

Steroid-type compounds and non-steroid-type compounds are already known as steroid $C_{17,20}$-lyase inhibitors. The steroid-type compounds are disclosed in, for example, WO 92/15404, WO 93/20097, EP-A 288053, EP-A 413270 and the like. As non-steroid-type compounds, for example, (1H-imidazol-1-yl)methyl-substituted benzimidazole derivatives are shown in Japanese Published Unexamined Patent Application No. 85975/1989, carbazole derivatives are shown in WO94/27989, WO96/14090 and WO97/00257, azole derivatives are shown in WO95/09157, 1H-benzimidazole derivatives are shown in U.S. Pat. No. 5,491,161, dihydronaphthalene derivatives are shown in WO99/18075, and naphthalene derivatives are shown in WO99/54309.

DESCRIPTION OF THE INVENTION

Heretofore, steroid $C_{17,20}$-lyase inhibitors usable for medical purposes have not been obtained, and an early development of steroid $C_{17,20}$-lyase inhibitors highly useful as medicine is awaited.

The present inventors have conducted intensive studies in an attempt to find a superior steroid $C_{17,20}$-lyase inhibitor, and found that compounds represented by the formulas (Ia) and (Ib) have, based on the specific chemical structure, unexpectedly superior pharmaceutical use, particularly a superior steroid $C_{17,20}$-lyase inhibitory activity, low toxicity and superior properties as a pharmaceutical product, and based on these findings, completed the present invention.

Accordingly, the present invention relates to (1) a compound represented by the formula:

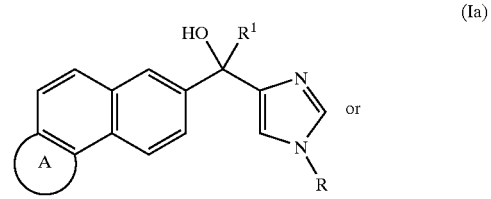

(Ia)

or

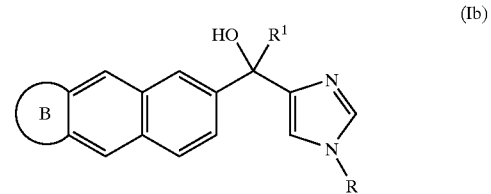

(Ib)

wherein R is a hydrogen atom or a protecting group, $R^1$ is a lower alkyl group or a cyclic alkyl group, and ring A and ring B are each an optionally substituted 5-membered or 6-membered ring having an amide bond in the ring (hereinafter also referred to as "compound (Ia)" or "compound (Ib)") or a salt thereof, (2) the compound of the aforementioned (1), wherein the ring A and ring B are each represented by the formula:

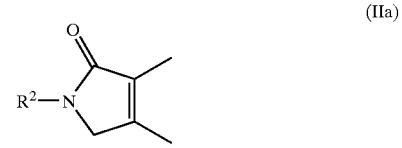

(IIa)

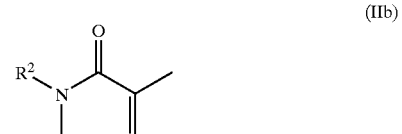

(IIb)

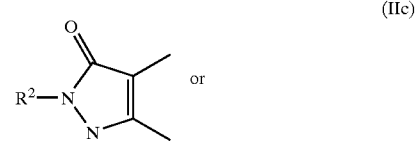

(IIc)

or

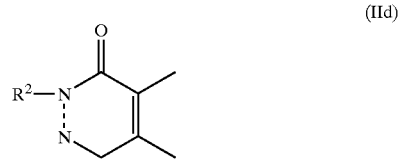

(IId)

wherein $R^2$ is a hydrogen atom, an optionally substituted hydrocarbon group or an optionally substituted amino group, and a dotted line indicates a single bond or a double bond when $R^2$ is a hydrogen atom, a single-bond when $R^2$ is an optionally substituted hydrocarbon group or an optionally substituted amino group, (3) a compound represented by the formula:

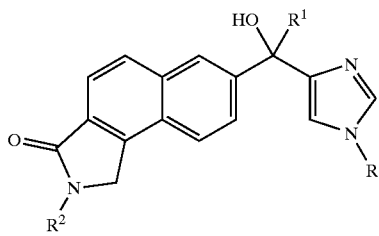

(III)

wherein each symbol is as defined above, or a salt thereof,
(4) a prodrug of a compound represented by the formula (Ia) or (Ib) or a salt thereof,
(5) a pharmaceutical composition containing a compound represented by the formula (Ia) or (Ib), or a salt thereof or a prodrug thereof,
(6) the composition of the aforementioned (5) which is a steroid $C_{17,20}$ lyase inhibitor,
(7) the composition of (5), which is an antitumor agent,
(8) the composition of (5), which is an agent for the prophylaxis or treatment of breast cancer or prostate cancer,
(9) an androgen reducer comprising a compound represented by the formula (Ia) or (Ib), a salt thereof or a prodrug thereof, and an LHRH modulator in combination,
(10) a production method of a compound represented by the formula:

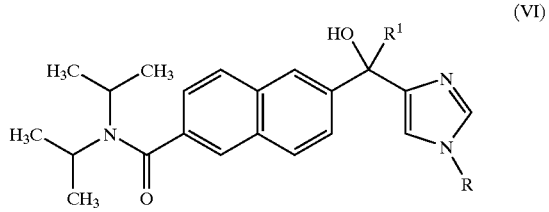

(VI)

wherein each symbol is as defined above, or a salt thereof, which comprises reacting a compound represented by the formula:

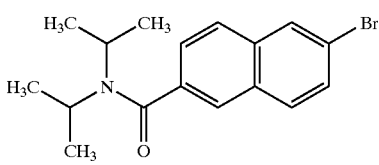

(IV)

with a compound represented by the formula:

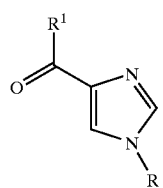

(V)

wherein each symbol is as defined above, or a salt thereof, in the presence of a base, and the like.

In the above-mentioned formulas (Ia) and (Ib), an optionally substituted 5-membered or 6-membered ring having an amide bond in the ring represented by ring A and ring B is exemplified by groups represented by the above-mentioned formulas (IIa), (IIb), (IIc) and (IId). The site of condensation of these rings and a naphthalene ring is the position represented by the formula (Ia) or (Ib), wherein the mode of binding may be any. For example, when ring A is represented by the formula (IIa) in a compound represented by the formula (Ia), the following two kinds of binding modes are shown:

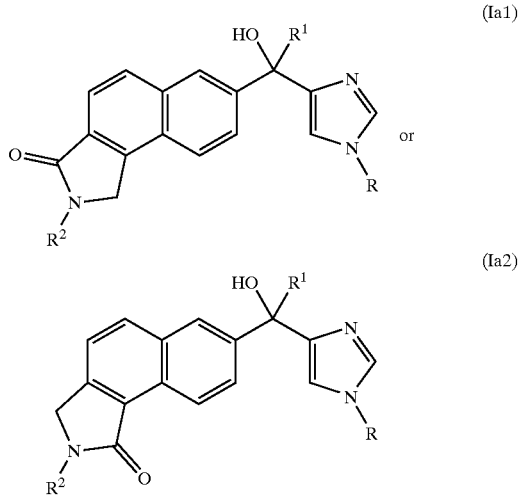

The compound represented by the formula (Ia) preferably has a binding mode of the formula (Ia1). The same applies when a compound represented by the formula (Ia) is condensed with a ring represented by the formula (IIb), (IIc) or (IId).

For example, when ring A is represented by the formula (IIa) in a compound represented by the formula (Ib), the following two kinds of binding modes are shown:

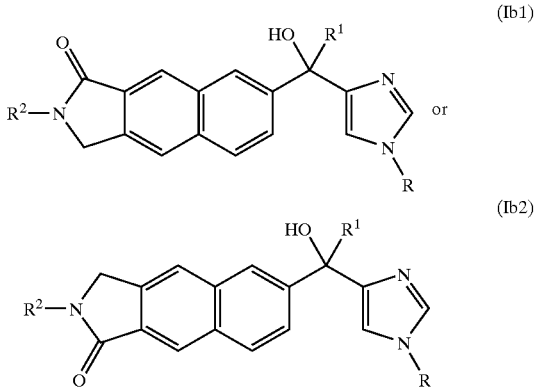

The same applies when a compound represented by the formula (Ib) is condensed with a ring represented by the formula (IIb), (IIc) or (IId).

In the above formulas (Ia), (Ib), (III), (V) and (VI), examples of the protecting group represented by R include $C_{1-6}$ alkylcarbonyl (e.g., acetyl, propionyl etc.), phenylcarbonyl, $C_{1-6}$ alkyl-oxycarbonyl (e.g., methoxycarbonyl, ethoxycarbonyl etc.), $C_{1-6}$ alkenyl-oxycarbonyl (e.g. allyloxycarbonyl etc.) phenyloxycarbonyl, $C_{7-10}$ aralkyloxy-carbonyl (e.g., phenyl-$C_{1-4}$ alkyloxy-carbonyl such as benzyloxycarbonyl etc. and the like), trityl, phthaloyl and N,N- dimethylaminomethylene and the like, each of which optionally having substituents, and formyl. Examples of the substituent include halogen atom (e.g., fluorine, chlorine, bromine, iodine etc.), formyl, $C_{1-6}$ alkyl-carbonyl (e.g., acetyl, propionyl, valeryl etc.), nitro group and the like, wherein the number of substituents is about 1 to 3.

In the above formulas (Ia), (Ib), (III), (V) and (VI), the lower alkyl group represented by $R^1$ is a straight chain or branched alkyl having 1 to 6 carbon atoms. Examples thereof include $C_{1-6}$ alkyl such as methyl, ethyl, n-propyl, isopropyl, n-butyl, isobutyl, sec-butyl, tert-butyl, n-pentyl, isopentyl, neopentyl, tert-pentyl, n-hexyl, isohexyl and the like. Examples of the cyclic alkyl group represented by $R^1$ include $C_{3-6}$ cycloalkyl such as cyclopropyl, cyclobutyl, cyclopentyl, cyclohexyl and the like, and the like. As $R^1$, $C_{1-4}$ alkyl (e.g., methyl, ethyl, n-propyl, isopropyl, n-butyl, sec-butyl, tert-butyl etc.) and the like are preferable.

In the formulas (IIa), (IIb), (IIc), (IId) and (III), examples of the optionally substituted amino group, which is represented by $R^2$, include unsubstituted amino, lower alkylamino (e.g., $C_{1-4}$ alkylamino such as methylamino, ethylamino, propylamino etc.), di-lower alkylamino (e.g., di-$C_{1-4}$ alkylamino such as dimethylamino, diethylamino etc.), $C_{1-4}$ alkanoylamino (e.g., acetylamino, propionylamino etc.), and the like.

In the formulas (IIa), (IIb), (IIc), (IId) and (III), examples of the hydrocarbon group of the optionally substituted hydrocarbon group, which is represented by $R^2$, include chain hydrocarbon group, cyclic hydrocarbon group and the like.

Examples of the chain hydrocarbon group include linear or branched chain hydrocarbon groups having 1 to 10 carbon atoms and the like, which are specifically alkyl, alkenyl, alkynyl and the like. Of these, alkyl is particularly preferable. Examples of the alkyl include $C_{1-10}$ alkyl, such as methyl, ethyl, n-propyl, isopropyl, n-butyl, isobutyl, sec-butyl, tert-butyl, n-pentyl, isopentyl, neopentyl, n-hexyl, isohexyl etc., and the like, with preference given to $C_{1-6}$ alkyl (e.g., methyl, ethyl, n-propyl, isopropyl, n-butyl, sec-butyl, tert-butyl etc.). Examples of the alkenyl include $C_{2-10}$ alkenyl, such as vinyl, 1-propenyl, allyl, isopropenyl, 1-butenyl, 2-butenyl, 3-butenyl, isobutenyl, sec-butenyl etc., and the like, with preference given to $C_{2-6}$ alkenyl (e.g., vinyl, 1-propenyl, allyl etc.). Examples of the alkynyl include $C_{2-10}$ alkynyl, such as ethynyl, 1-propynyl, propargyl etc., and the like, with preference given to $C_{2-6}$ alkynyl (e.g., ethynyl etc.).

Examples of the cyclic hydrocarbon group include cyclic hydrocarbon groups having 3 to 18 carbon atoms, such as alicyclic hydrocarbon groups, aromatic hydrocarbon groups and the like.

Examples of the alicyclic hydrocarbon group include monocyclic groups consisting of 3 to 10 carbon atoms and condensed polycyclic groups, such as cycloalkyl, cycloalkenyl and the like, and bicyclic or tricyclic condensed rings of these and aromatic hydrocarbon having 6 to 14 carbon atoms (e.g., benzene etc.) and the like. Examples of the cycloalkyl include $C_{3-6}$ cycloalkyl, such as cyclopropyl, cyclobutyl, cyclopentyl, cyclohexyl etc., and the like and examples of the cycloalkenyl include $C_{3-6}$ cycloalkenyl, such as cyclopropenyl, cyclobutenyl, cyclopentenyl, cyclohexenyl etc., and the like.

Examples of the aromatic hydrocarbon group include monocyclic aromatic hydrocarbon groups, condensed polycyclic aromatic hydrocarbon groups and the like consisting of 6 to 18 carbon atoms, which are specifically $C_{6-14}$ aryl, such as phenyl, 1-naphthyl, 2-naphthyl, 2-indenyl, 2-anthryl and the like, with preference given to $C_{6-10}$ aryl (e.g., phenyl etc.) and the like.

The substituent that the chain hydrocarbon group may have in the optionally substituted hydrocarbon group is not subject to any particular limitation. Examples thereof include halogen atom, hydroxyl, alkoxy, acyloxy, alkylthio, acylamino, carboxyl, alkoxycarbonyl, oxo, alkylcarbonyl, cycloalkyl, aryl, aromatic heterocyclic group and the like. These substituents are substituted in a chemically acceptable range on the chain hydrocarbon group, wherein the number of substitutions by the substituent is 1 to 5, preferably 1 to 3. When the number of substituents is not less than 2, they may be the same or different.

The substituent that the cyclic hydrocarbon group may have in the optionally substituted hydrocarbon group is not subject to any particular limitation. Examples thereof include halogen atom, hydroxyl, alkoxy, acyloxy, alkylthio, alkylsulfonyl, mono- or di-alkylamino, acylamino, carboxyl, alkoxycarbonyl, alkynylcarbonyl, alkyl, cycloalkyl, aryl, aromatic heterocyclic group and the like. These substituents are substituted in a chemically acceptable range on the cyclic hydrocarbon group, wherein the number of substitutions by the substituent is 1 to 5, preferably 1 to 3. When the number of substituents is not less than 2, they may be the same or different.

Examples of the halogen atom include fluorine, chlorine, bromine, iodine and the like. Examples of the alkoxy include $C_{1-10}$ alkoxy, such as methoxy, ethoxy, propoxy, isopropoxy, butoxy, isobutoxy, sec-butoxy, pentyloxy, hexyloxy etc., and the like. Examples of the acyloxy include formyloxy, $C_{1-10}$ alkyl-carbonyloxy (e.g., acetoxy, propionyloxy etc.) and the like. Examples of the alkylthio include $C_{1-10}$ alkylthio, such as methylthio, ethylthio, propylthio, isopropylthio etc., and the like. Examples of the alkylsulfonyl include $C_{1-10}$ alkylsulfonyl groups, such as methylsulfonyl, ethylsulfonyl, propylsulfonyl etc., and the like. Examples of the mono- or di-alkylamino include those similar to the aforementioned $C_{1-4}$ alkylamino, such as methylamino, ethylamino, propylamino etc., and di-$C_{1-4}$ alkylamino such as dimethylamino, diethylamino etc, and the like. Examples of the acylamino include formylamino, diformylamino, mono- or di-$C_{1-10}$ alkyl-carbonylamino (e.g., acetylamino, propionylamino, butyrylamino, diacetylamino etc.) and the like. Examples of the alkoxycarbonyl include $C_{1-10}$ alkoxy-carbonyl, such as methoxycarbonyl, ethoxycarbonyl, propoxycarbonyl, isopropoxycarbonyl, butoxycarbonyl etc., and the like. Examples of the alkylcarbonyl include $C_{1-10}$ alkyl-carbonyl, such as acetyl, propionyl, butyryl, valeryl etc., and the like. Examples of the alkynylcarbonyl include $C_{3-10}$ alkynylcarbonyl group, such as acetylenylcarbonyl, 1-propynylcarbonyl, 2-propynylcarbonyl etc., and the like. Examples of the cycloalkyl include $C_{3-10}$ cycloalkyl, such as cyclopropyl, cyclobutyl, cyclopentyl, cyclohexyl etc., and the like. Examples of the aryl include $C_{6-14}$ aryl, such as phenyl, 1-naphthtyl, 2-naphthtyl etc., and the like. Examples of the aromatic heterocyclic group include 5 to 10-membered mono- to tri-cyclic aromatic heterocyclic groups containing, besides the carbon atom, 1 or 2 kinds of hetero atoms selected from nitrogen, oxygen and sulfur, and the like. The total number of hetero atoms contained in the aromatic heterocyclic group is preferably 1 to 4. Specifically, for example, thienyl, pyridyl, furylpyrazinyl, pyrimidinyl, imidazolyl, pyrazolyl, thiazolyl, isothiazolyl, oxazolyl, isoxazolyl, pyridazinyl, tetrazolyl, quinolyl, indolyl, isoindolyl and the like are mentioned. Examples of the alkyl include $C_{1-10}$ alkyl, such as methyl, ethyl, propyl, isopropyl, butyl, sec-butyl, tert-butyl, pentyl etc., and the like.

Preferable examples of compound (Ia) or compound (Ib) of the present invention include the following compounds. (1) 7-[1-hydroxy-1-(1H-imidazol-4-yl)-2-methylpropyl]-2-methyl-1,2-dihydro-3H-benzo[e]isoindol-3-one, (2) 7-[1-hydroxy-1-(1H-imidazol-4-yl)-2-methylpropyl]-1,2-dihydro-3H-benzo[e]isoindol-3-one, (3) 2-ethyl-7-[1-hydroxy-1-(1H-imidazol-4-yl)-2-methylpropyl]-1,2-dihydro-3H-benzo[e]isoindol-3-one, (4) 7-[1-hydroxy-1-(1H-imidazol-4-yl)-3-methylbutyl]-2-methyl-1,2-dihydro-3H-benzo[e]isoindol-3-one.

The compounds (Ia) and (Ib) of the present invention may form a salt. Examples of the salt include acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) and the like. When compound (Ia) and compound (Ib) have an acidic group, such as carboxyl group and the like, they may form a salt with a base. Examples of such salt include salts with inorganic base (e.g., alkali metals such as sodium, potassium etc.; alkaline earth metals such as calcium, magnesium etc.; transition metals such as zinc, iron, copper etc., and the like); salts with organic base (e.g., organic amines such as trimethylamine, triethylamine, pyridine, picoline, ethanolamine, diethanolamine, triethanolamine, dicyclohexylamine, N,N'-dibenzylethylenediamine etc., basic amino acids such as arginine, lysine, ornithine etc., etc.), and the like.

The compounds (Ia) and (Ib) and a salt thereof may be hydrates. In the following, compounds (Ia) and (Ib) and salts and hydrates thereof are referred to as compound (I).

The prodrug of compound (I) means a compound which is converted to compound (I) having a steroid $C_{17,20}$-lyase inhibitory activity by in vivo reactions of enzymes, gastric acid and the like.

Examples of the prodrug of compound (I) include a compound obtained by substituting a nitrogen atom of imidazole of compound (I) with acyl or alkyl (e.g., compound wherein the nitrogen atom has been substituted with dimethylaminosulfonyl, acetoxymethyl, (5-methyl-2-oxo-1,3-dioxolen-4-yl)methoxycarbonylmethyl, pivaloyloxymethyl, benzyloxymethyl etc.); a compound obtained by substituting the hydroxy group of compound (I) with acyl, alkyl, phosphate, sulfate or borate, (e.g., compound (I) wherein the hydroxy group has been substituted with acetyl, palmitoyl, propanoyl, pivaloyl, succinyl, fumaryl, alanyl, dimethylaminomethylcarbonyl etc.); and the like. These compounds can be produced by a method known per se.

The prodrug of compound (I) may be as it is or a pharmaceutically acceptable salt. When the prodrug of compound (I) has an acidic group such as a carboxyl group, examples of the salt include salts with inorganic base (e.g., alkali metals such as sodium, potassium etc.; alkaline earth metals such as calcium, magnesium etc.; transition metals such as zinc, iron, copper etc., and the like); organic bases (e.g., organic amines such as trimethylamine, triethylamine, pyridine, picoline, ethanolamine, diethanolamine, triethanolamine, dicyclohexylamine, N,N'-dibenzylethylenediamine etc.; basic amino acids such as arginine, lysine, ornithine etc., and the like), and the like.

When the prodrug of compound (I) has a basic group such as an amino group and the like, examples of the salt include salt with inorganic acid or organic acid (e.g., hydrochloric acid, nitric acid, sulfuric acid, phosphoric acid, carbonic acid, bicarbonate acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.); acidic amino acids such as aspartic acid, glutamic acid etc.; and the like.

In addition, the prodrug of compound (I) may be a hydrate or a non-hydrate.

Compound (I) may have one or more asymmetric carbons in the molecule. The compound of the present invention also encompasses R-configuration and S-configuration at the asymmetric carbons.

As the compound (I), a compound having an absolute configuration of S configuration and a carbon atom bonded with a hydroxy group is preferable.

Throughout the specification, of the compounds represented by the formulas (III) and (VI), a compound having a basic group or an acidic group can form a salt with an acid or a salt with a base, respectively. Examples of the salt with an acid and the salt with a base include those similar to the salts of the compound (I) mentioned above. Hereinafter the compounds represented by each formula and its salt are referred to as compound (symbol of formula). For example, a compound of formula (III) and a salt thereof are simply referred to as compound (III). The compound of the formula (VI) and a salt thereof are simply referred to as compound (VI).

The compound (I) can be produced by, for example, the following production methods shown as regards compound (III), compound (IIIa), compound (VII) and compound (VIIa) and the like.

The starting compound and synthetic intermediates can be used in a free form or as a salt thereof like compound (I), and they may be used for a reaction as a reaction mixture or after isolation by a known method.

The compound (III) and compound (IIIa) are produced by, for example, a method shown in the following and the like.

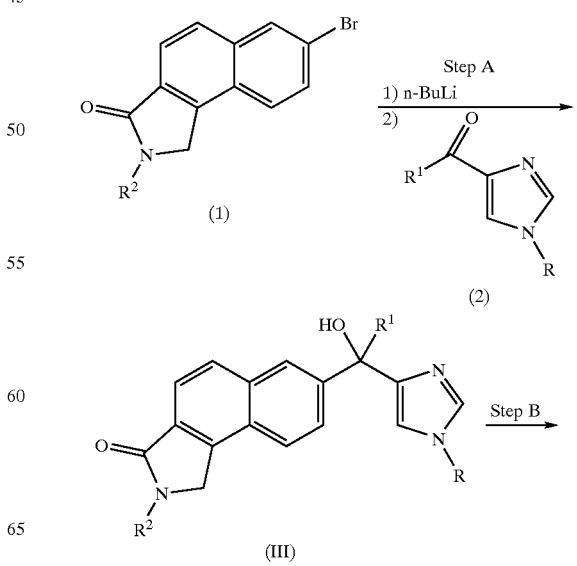

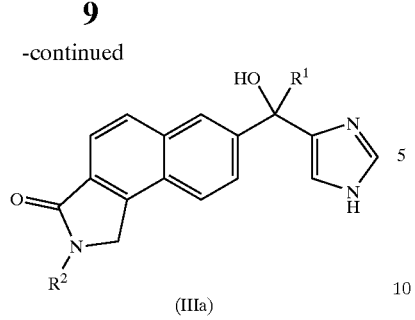

(IIIa)

wherein each symbol is as defined above,

[Step A]

The compound (1) is reacted with n-butyllithium to convert the compound to a lithium salt, which is then reacted with compound (V) to give compound (III).

The amount of n-butyllithium to be used in this reaction is 1–4 moles, preferably 2–2.5 moles, per 1 mole of the starting compound (1). The reaction temperature for the reaction of n-butyllithium is −100° C. to 0° C., preferably −80° C. to −20° C. The reaction time is about 5 min. to 20 hrs. This reaction is generally carried out in an organic solvent that does not affect the reaction. As the organic solvent that does not adversely affect the reaction, ethers such as diethyl ether, dioxane, tetrahydrofuran (THF) and the like, saturated hydrocarbons such as hexane, pentane and the like, halogenated hydrocarbons such as dichloromethane, chloroform and the like, aromatic hydrocarbons such as benzene, toluene and the like, and the like are used. These may be used alone or as a mixture of two or more kinds thereof mixed at a suitable ratio. The compound (V) is used in an amount of 0.1–10 equivalents, preferably 0.2–2 equivalents, relative to compound (1).

[Step B]

When R of compound (III) is a protecting group, the protecting group is removed by a method known per se or a method analogous thereto to give compound (IIIa). For example, when R is a trityl group, the trityl group can be removed by a treatment under acidic conditions or hydrogenolysis. As the acid, an organic acid such as formic acid, acetic acid and the like, an inorganic acid such as hydrochloric acid and the like, and the like can be used. The reaction can be carried out using a solvent inert to the reaction such as alcohols, ethers (e.g., THF etc.), and the like. The reaction temperature is generally 0–100° C.

The compound (III) is produced by, for example, the following method.

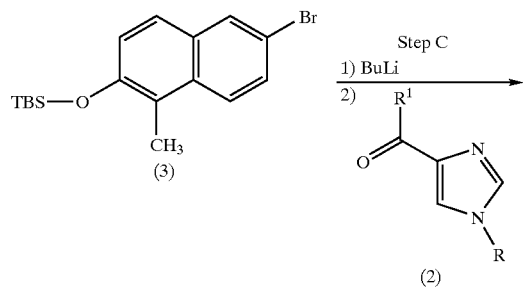

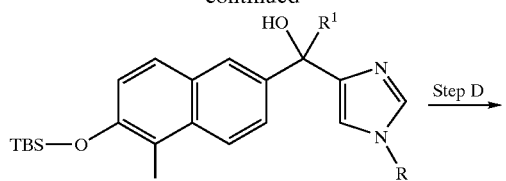

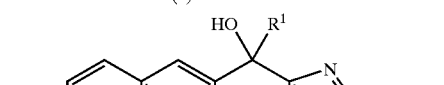

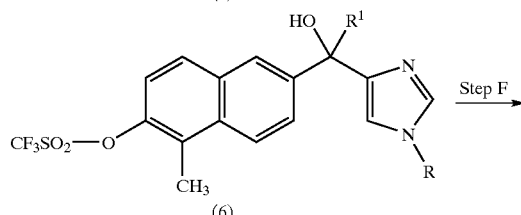

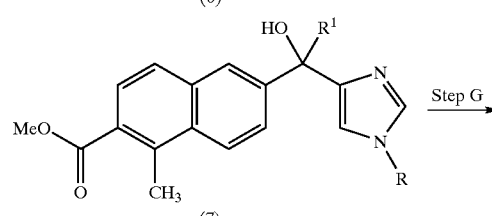

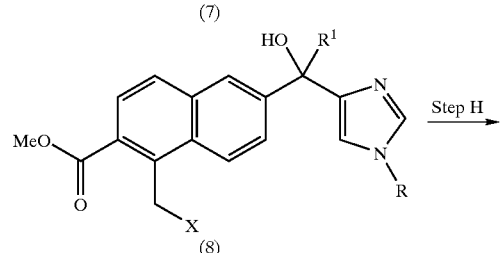

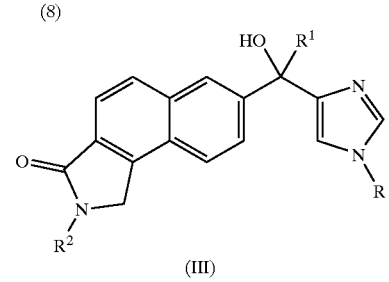

(III)

wherein X is a halogen atom and other symbols are as defined above.

[Step C]

This is a step wherein compound (3) is reacted with n-butyllithium to convert the compound to a lithium salt, which is then reacted with compound (V) to give compound (4).

The amount of n-butyllithium to be used in this reaction is 1–3 moles, preferably 1–1.5 moles, per 1 mole of the starting compound (3). The reaction temperature for the reaction of n-butyllithium is −100° C. to 0° C., preferably −80° C. to −20° C. The reaction time is about 5 min. to 20 hrs. This reaction is generally carried out in an organic solvent that does not affect the reaction. As the organic solvent that does not adversely affect the reaction, ethers such as diethyl ether, dioxane, THF and the like, saturated hydrocarbons such as hexane, pentane and the like, halogenated hydrocarbons such as dichloromethane, chloroform and the like, aromatic hydrocarbons such as benzene, toluene and the like, and the like are used. These may be used alone or as a mixture of two or more kinds thereof mixed at a suitable ratio. The compound (V) is used in an amount of 0.1–10 equivalents, preferably 0.2–2 equivalents, relative to compound (3).

[Step D]

This is a step wherein compound (4) is reacted with tetrabutylammonium fluoride (TBAF) and the like and a tert-butyldimethylsilyl (TBS) group is removed to give compound (5). The reaction is carried out according to a conventional method. (Reference: Protecting Groups in Organic Synthesis, $2^{nd}$ Edition, edited by T. W. Greene and P. G. M. Wuts, John Wiley & Sons, Inc. 1991)

[Step E]

This is a step wherein compound (5) is reacted with trifluoromethanesulfonic anhydride ($Tf_2O$) in the presence of a base to give compound (6). As the base to be used for this reaction, pyridine, lutidine, triethylamine, ethyldiisopropylamine and the like are used, wherein pyridine is particularly preferable. The reaction temperature is –50° C. to 50° C., preferably –10° C. to 20° C. The reaction time is about 30 min. to 20 hrs. For the reaction, a solvent that does not adversely affect the reaction can be used, and examples thereof include THF, dichloromethane and the like. The amount of trifluoromethanesulfonic anhydride to be used is 0.8–2 moles, preferably 1–1.3 moles, per 1 mole of compound (5).

[Step F]

This is a step wherein compound (6) is reacted with carbon monoxide and methanol in the presence of a palladium catalyst to give compound (7). The reaction can be carried out according to a method described in a reference (S. Cacchi et al., Tetrahedron Lett. 1986, Vol. 27, pp. 3931–3934).

Examples of the palladium catalyst to be used include (1,1'-bis(diphenylphosphino)ferrocene)dichloropalladium and the like. The reaction temperature is 30° C.–150° C., preferably 60° C.–120° C. The reaction time is about 1–50 hrs. As the solvent to be used, dimethylformamide (DMF) and the like are preferable.

[Step G]

This is a step wherein. compound (7) is reacted with a halogenating agent to give compound (8). Examples of the halogenating agent include N-bromosuccinimide, N-chlorosuccinimide and the like. For this reaction, a reaction initiator is generally used. Examples of the reaction initiator include 2,2'-azobisisobutyronitrile and the like. The reaction temperature is 20° C.–150° C., preferably 50° C.–120° C. The reaction time is about 30 min.–20 hrs. This reaction is generally carried out in a solvent that does not adversely affect the reaction. Examples of the preferable solvent include halogenated hydrocarbons such as chloroform, carbon tetrachloride, chlorobenzene and the like, carbon disulfide, ethyl acetate and the like. The halogenating agent such as N-bromosuccinimide and the like is used in an amount of 0.5–3 moles, preferably 1–2 moles, per 1 mole of compound (7).

[Step H]

This is a step wherein compound (8) is reacted with the corresponding amines, then intramolecularly cyclized. The reaction temperature is 0° C.–100° C., preferably 20° C.–60° C. The reaction time is about 30 min.–48 hrs. The reaction is carried out without solvent or in a solvent that does not adversely affect the reaction. The solvent that does not adversely affect the reaction includes alcohols such as methanol and the like, THF, toluene and the like.

The compound (III) can be also produced by, for example, a method shown in the following.

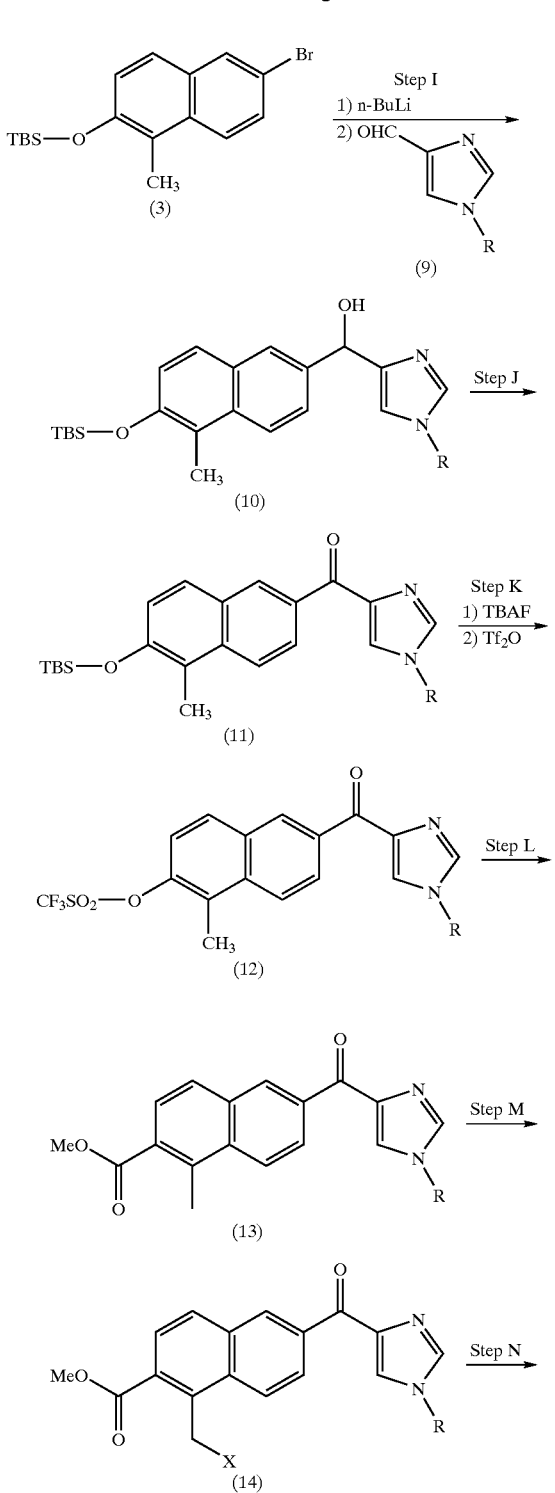

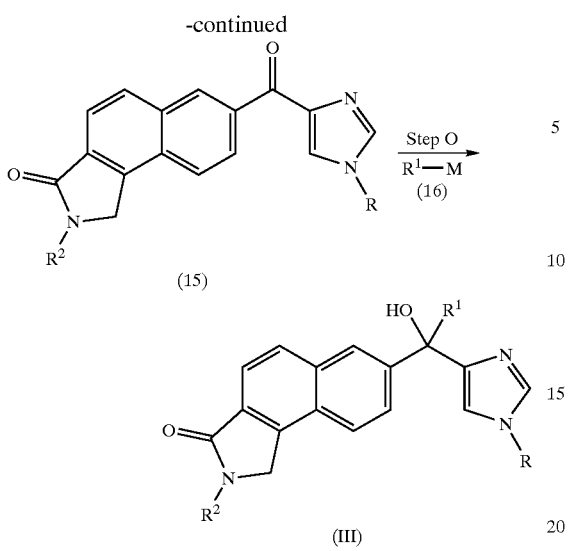

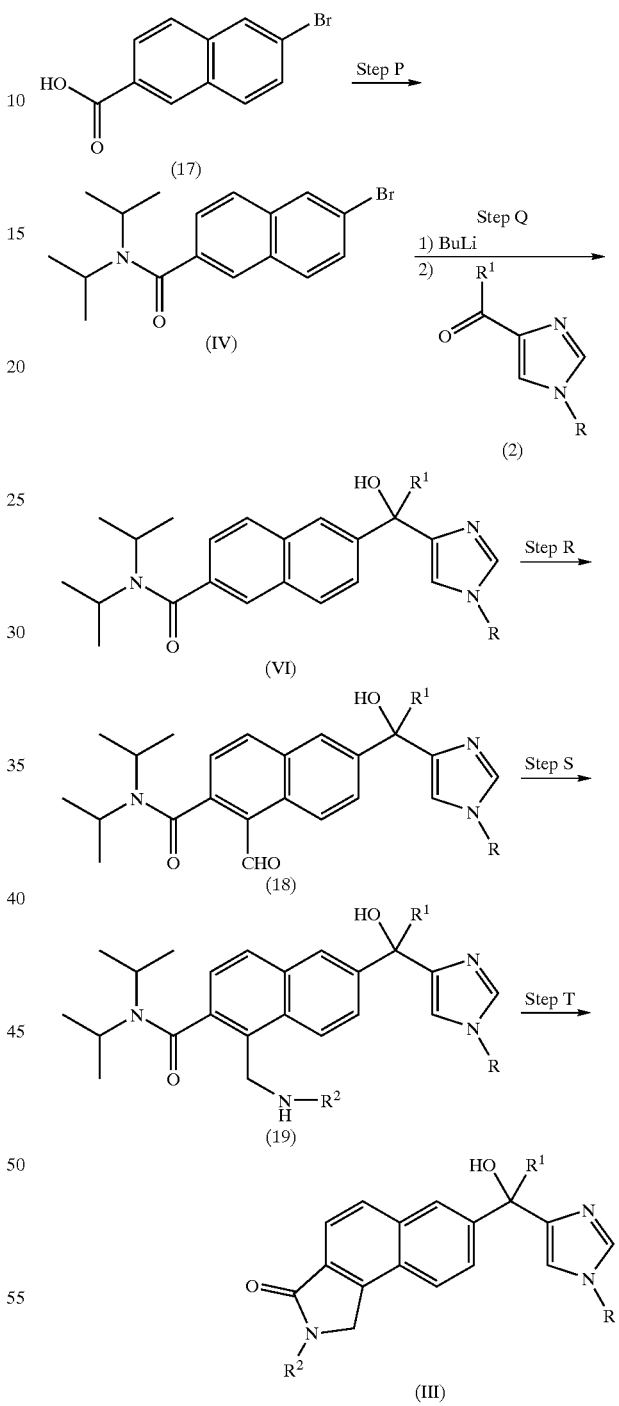

wherein M is a metal or a salt thereof and other symbols are as defined above.

Examples of the metal represented by M include lithium, magnesium and the like, and examples of the metal salt include metal halides such as magnesium chloride, magnesium bromide and the like, and the like.

[Step I]

This is a step wherein compound (3) is reacted with n-butyllithium to convert the compound to a lithium salt, which is then reacted with compound (9) to give compound (10). The reaction is carried out under the same conditions as in Step C.

[Step J]

This is a step wherein compound (10) is oxidized to convert to compound (11). As the oxidant, manganese dioxide and the like are preferable. The reaction temperature is 0° C.–100° C., preferably 20° C.–60° C. The reaction time is about 1 hr.–48 hrs. This reaction is carried out in a solvent that does not adversely affect the reaction. Examples of the solvent that does not adversely affect the reaction include halogenated hydrocarbon such as dichloromethane and the like, DMF and the like.

[Step K]

This is a step wherein compound (11) is de-tert-butyldimethylsilylated and then converted to trifluoromethanesulfonic acid ester. This reaction can be carried out under the same reaction conditions as in the above-mentioned Step D and Step E.

[Step L, M, N]

These steps correspond to the above-mentioned steps F, G and H, respectively, and can be carried out under the same reaction conditions.

[Step O]

This is a step wherein compound (15) is reacted with the corresponding organic metal compound (16) to give compound (III). The reaction temperature is 40° C.–60° C., preferably −20° C.–40° C. The reaction time is about 5 min.–20 hrs. This reaction is generally carried out in an organic solvent that does not adversely affect the reaction. Examples of the organic solvent that does not adversely affect the reaction include ethers such as diethyl ether, dioxane, THF and the like, saturated hydrocarbons such as hexane, pentane and the like, halogenated hydrocarbons such as dichloromethane, chloroform and the like, aromatic hydrocarbons such as benzene, toluene and the like. These may be used alone or as a mixture of two or more kinds thereof mixed at a suitable ratio. The amount of compound (16) is 1–10 moles, preferably 1–3 moles, relative to compound (15).

The compound (III) is also produced by, for example, the method shown in the following.

wherein each symbol is as defined above.

[Step P]

This is a step wherein compound (17) is converted to compound (IV). The compound (17) is converted to an acid chloride by the action of chloride such as thionyl chloride and the like, which is then reacted with diisopropylamine to give compound (IV). It is also possible to obtain compound (IV) by reacting compound (17) with diisopropylamine in the presence of an activator such as dicyclohexylcarbodiimide and the like.

[Step Q]

This is a step wherein compound (IV) is reacted with compound (V) in the presence of a base to give compound (VI). As the base, for example, n-butyllithium, sec-butyllithium, tert-butyllithium and the like can be mentioned, with preference given to n-butyllithium. When n-butyllithium is used as a base, for example, compound (IV) is reacted with n-butyllithium to convert the compound to a lithium salt, which is then reacted with compound (V) to give compound (VI).

The amount of the base to be used in this reaction is 1–3 moles, preferably 1–1.5 moles, per 1 mole of the starting compound (IV). When a base is to be reacted, the reaction temperature is −100° C. to 0° C., preferably −80° C. to −20° C. The reaction time is about 5 min.–20 hrs. This reaction is generally carried out in an organic solvent that does not affect the reaction. Examples of the organic solvent that does not adversely affect the reaction include ethers such as diethyl ether, dioxane, THF and the like, saturated hydrocarbons such as hexane, pentane and the like, halogenated hydrocarbons such as dichloromethane, chloroform and the like, aromatic hydrocarbons such as benzene, toluene and the like, and the like. These may be used alone or as a mixture of two or more kinds thereof mixed at a suitable ratio. The compound (V) is used in an amount of 0.1–10 equivalents, preferably 0.2–2 equivalents, relative to compound (IV).

[Step R]

This is a step wherein compound (VI) is reacted with alkyllithium and the like to convert the compound to a lithium salt, which is then formylated to give compound (18). Examples of alkyllithium to be used in this reaction include $C_{1-4}$ alkyllithium such as n-butyllithium, sec-butyllithium, tert-butyllithium and the like, with particular preference given to n-butyllithium. The amount of alkyllithium to be used is 2–4 moles, preferably 2–2.5 moles, per 1 mole of the starting compound (VI). When alkyllithium is reacted, the reaction temperature is −100° C. to 0° C., preferably −80° C. to −20° C. As the starting compound having a formyl group, DMF is preferable.

The amount thereof to be used is 2–20 moles, preferably 3–10 moles, per 1 mole of compound (VI).

[Step S]

This is a step wherein compound (18) is reacted with amines under reducing conditions to give compound (19). The amount of amines is 1–20 moles, preferably 1–5 moles, per 1 mole of compound (18). Examples of the reducing agent include sodium borohydride, sodium triacetoxyborohydride, sodium cyanoborohydride and the like. The amount thereof to be used is 1–5 moles, preferably 2–4 moles, per 1 mole of compound (18). The reaction temperature is 0° C.–50° C., preferably 10° C.–30° C. The reaction time is about 1 hr–20 hrs.

[Step T]

This is a step wherein compound (19) is intramolecularly cyclized in the presence of a base. As the base, alkyllithiums (e.g., butyllithium, lithium diisopropylamide and the like) are preferable. The reaction temperature is −80° C.–10° C., preferably −50° C.–10° C. The reaction time is about 5 min.–5 hrs. The reaction is carried out without solvent or in a solvent that does not adversely affect the reaction. Examples of the solvent that does not adversely affect the reaction include THF, toluene and the like.

The compound (VII) can be produced by, for example, a method shown in the following.

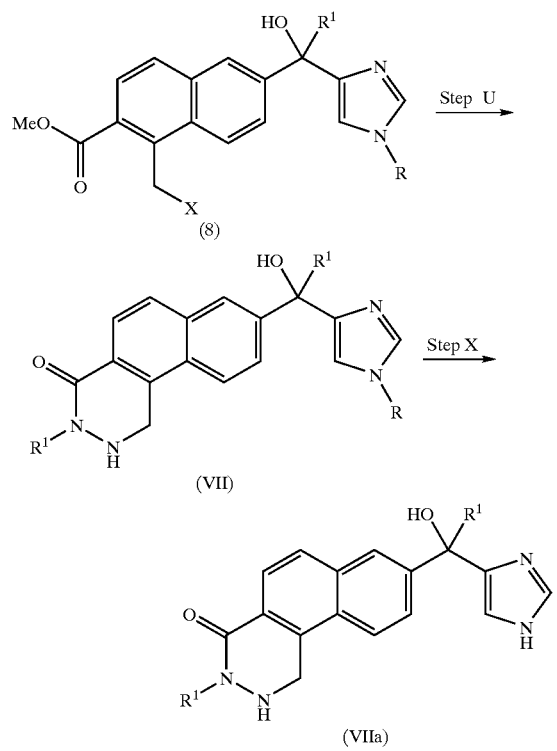

wherein each symbol is as defined above.

[Step U]

This is a step wherein compound (8) is reacted with the corresponding hydrazine and then intramolecularly cyclized. The reaction temperature is 0° C.–100° C., preferably 20° C.–60° C. The reaction time is about 30 min.–48 hrs. The reaction is carried out without solvent or in a solvent that does not adversely affect the reaction. Examples of the solvent that does not adversely affect the reaction include alcohols such as methanol and the like, THF, toluene and the like.

[Step X]

When R of compound (VII) is a protecting group, the protecting group is removed by a method known per se, or a method analogous thereto, to give compound (VIIa). The reaction can be carried out under the same conditions as in step B.

The compound (1) can be produced by, for example, a method shown in the following.

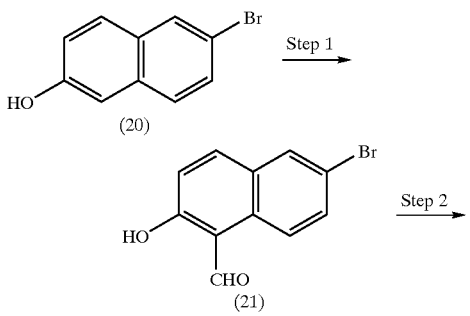

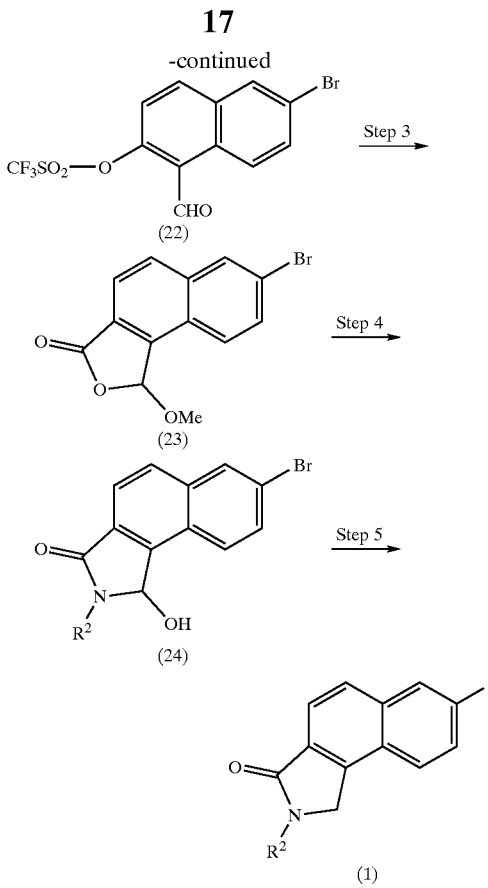

wherein each symbol is as defined above.

[Step 1]

This is a step wherein compound (20) is reacted with DMF, dichloromethylmethyl ether and the like in the presence of an acid catalyst to give compound (21). As the acid catalyst, a Lewis acid such as titanium tetrachloride and the like is preferable. The reaction temperature is −70° C.–100° C., preferably 0° C.–30° C. The reaction time is about 5 min.–24 hrs. This reaction is generally carried out in a solvent that does not adversely affect the reaction. As the solvent that does not adversely affect the reaction, dichloromethane, toluene and the like can be mentioned.

[Step 2]

This step can be performed according to the reaction conditions of Step E. In this reaction, bis(trifluoromethanesulfonyl)anilide and the like can be used besides trifluoromethanesulfonic acid anhydride as an acylating gent.

[Step 3]

This step is a reaction for insertion of carbon monoxide, which can carried out using the same catalyst and the same reaction conditions as in Step F.

[Step 4]

This is a step wherein compound (23) is reacted with the corresponding amine to give compound (24). The amount of amine to be used is preferably in great excess relative to compound (24). The reaction temperature is −70° C.–100° C., preferably −20° C.–50° C. The reaction time is about 1 min.–24 hrs. This reaction can be also carried out in a solvent that does not adversely affect the reaction. Examples of the solvent that does not adversely affect the reaction include THF, methanol and the like.

[Step 5]

This is a step wherein compound (24) is reduced to give compound (1). As the reducing agent, zinc, iron and the like can be used, wherein zinc is particularly preferable. The reaction is generally carried out in acetic acid. The reaction temperature is 0° C.–120° C., preferably 50° C.–110° C. The reaction time is about 5 min.–24 hrs.

The compounds (IIIa) and (VIIa) are subjected to optical resolution by a method known per se or a method analogous thereto to give optically active compounds. The method for the optical resolution includes liquid chromatography methods using an optically active column, diastereomer salt methods using an optically active acid or base, and the like.

The compound (I) can be efficiently resolved optically by using an optically active column (e.g., CHIRALPAK AD manufactured by Daicel Chemical Industries). In addition, a desired optically active form can be separated by forming a diastereomer salt with an optically active acid and utilizing the difference in the solubility.

When the desired compound is obtained in a free form by the above reactions, the compound may be converted to a salt by a conventional method. When the desired compound is obtained as a salt, the compound can be converted to a free form or a different salt by a conventional method. The compound (I) thus obtained can be isolated from the reaction mixture and purified by known procedures such as phase transfer, concentration, solvent extraction, fractional distillation, crystallization, recrystallization, chromatography and the like.

In addition, a protecting group may be used for amino group, carboxyl group, and hydroxy group in the compound or a salt thereof to be reacted in the above reactions, which are not involved in the reaction. A protecting group may be added or removed by a known method.

As the protecting group of the amino group, for example, $C_{1-6}$ alkylcarbonyl (e.g., acetyl, propionyl etc.), phenylcarbonyl, $C_{1-6}$ alkyl-oxycarbonyl (e.g., methoxycarbonyl, ethoxycarbonyl etc.), phenyloxycarbonyl, $C_{7-10}$ aralkyloxycarbonyl (e.g., phenyl-$C_{1-4}$ alkyloxy-carbonyl such as benzyloxycarbonyl etc., and the like), trityl, phthaloyl, N,N-dimethylaminomethylene and the like are used, each of which may have substituents, and formyl. As the substituent, for example, halogen atom, formyl, $C_{1-6}$ alkyl-carbonyl, nitro and the like are used. The number of substituent is about 1 to 3.

As the protecting group of carboxyl group, for example, $C_{1-6}$ alkyl, phenyl, trityl, silyl and the like are used, each of which may have substituents. Examples of the substituent include halogen atom, formyl, $C_{1-6}$ alkyl-carbonyl, nitro and the like. The number of substituents is about 1 to 3.

As the protecting group of hydroxy group, for example, $C_{1-6}$ alkyl, phenyl, $C_{7-10}$ aralkyl, formyl, $C_{1-6}$ alkyl-carbonyl, phenyloxycarbonyl, benzoyl, ($C_{7-10}$ aralkyloxy)carbonyl, pyranyl, furanyl, silyl and the like are used, each of which may have substituents. As the substituent, for example, halogen atom, $C_{1-6}$ alkyl, phenyl, $C_{7-10}$ aralkyl (e.g., phenyl-$C_{1-4}$ alkyl such as benzyl etc.), nitro and the like are used. The number of substituents is about 1 to 4.

The protecting group can be removed by a method known per se or a similar method. Examples of the method include treatments using, for example, acid, base, reduction, ultraviolet light, hydrazine, phenylhydrazine, sodium N-methyldithiocarbamate, tetrabutylammonium fluoride, palladium acetate and the like.

The compound (I) can be obtained as stable crystals by forming a salt with an acid. This salt has higher solubility in water and shows superior oral absorption.

The compound (I) and a prodrug thereof (hereinafter to be referred to as compound of the present invention) have a superior effect as a medicine, and especially have a superior inhibitory activity against steroid $C_{17,20}$-lyase. The compound of the present invention is low toxic and causes few side effects. Therefore, the compound is useful as, for example, (i) an androgen or estrogen reducer, and (ii) an agent for the prophylaxis or treatment of various androgen- or estrogen-related diseases, such as (1) primary cancer, metastasis or recurrence of malignant tumor (e.g., prostate cancer, breast cancer, uterine cancer, ovarian cancer etc.), (2) various symptoms accompany these cancers (e.g., pain, cachexia etc.), (3) prostatic hypertrophy, virilism, hirsutism, male pattern alopecia, precocious puberty, endometriosis, uterus myoma, adenomyosis of uterus, mastopathy, polycystic ovary syndrome etc. in a mammal (e.g., human, bovine, horse, pig, dog, cat, monkey, mouse, rat etc., especially human).

While the compound of the present invention has a superior effect even when used solely, the effect can be further promoted by using the compound in combination with other pharmaceutical preparations and therapies. Examples of the preparation and therapy to be combined include, but not limited to, hormone-related agents such as sex hormone agent and the like, alkylating agents, antimetabolites, antitumor antibiotics, plant alkaloids, immunotherapies and the like.

Examples of hormone-related agent include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (e.g., tamoxifen citrate, toremifene citrate etc.), contraceptive pill, mepitiostane, testolactone, aminoglutethimide, LHRH (luteinizing hormone releasing hormone) modulator, [LHRH agonists (e.g., goserelin acetate, buserelin, leuprorelin etc.), LHRH antagonists (e.g., ganirelix, cetrorelix, abarelix etc.)], droloxifene, epitiostanol, ethinylestradiol sulfonate, aromatase inhibitors (e.g., fadrozole hydrochloride, anastrozole, letrozole, exemestane, vorozole, formestane etc.), anti-androgens (e.g., flutamide, bicalutamide, nilutamide etc.), 5α-reductase inhibitors (e.g., finasteride, epristeride etc.), adrenocortical hormones (e.g., cortisol, dexamethasone, prednisolone, betamethasone, triamcinolone etc.), inhibitors of androgen-synthesis (e.g., abiraterone etc.), retinoid and suppressing agents of retinoid metabolism (e.g., liarozole etc.), and the like.

Examples of alkylating agents include nitrogen mustard, nitrogen mustard N-oxide hydrochloride, chlorambucil, cyclophosphamide, ifosfamide, thiotepa, carboquone, improsulphan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, ethoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulfan, trofosfamide, zinostatin stimalamer, adozelesin, cystemustine, bizelesin, and the like.

Examples of antimetabolites include mercaptopurine, 6-mercaptopurine riboside, thioinosine, methotrexate, enocitabine, cytarabine, cytarabine ocfosfate, ancitabine hydrochloride, 5-FU analogues (e.g., fluorouracil, tegafur, UFT, doxifluridine, carmofur, galocitabine, emitefur etc.), aminopterin, leucovorin calcium, tabloid, butocin, calcium folinate, calcium levofolinate, cladribine, fludarabine, gemcitabine, hydroxycarbamide, pentostatin, piritrexim, idoxuridine, mitoguazone, tiazofurin and the like.

Example of antitumor antibiotics include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and the like.

Examples of plant alkaloids include etoposide, etoposide phosphate, vinblastine sulfate, vincristine sulfate, vindesine sulfate, teniposide, paclitaxel, vinorelbine, and the like.

Examples of immunotherapeutic agent (BRM) include picibanil, krestin, sizofiran, lentinan, ubenimex, interferons, interleukins, macrophage-colony stimulating factor, granulocyte-colony stimulating factor, erythropoietin, lymphotoxin, BCG vaccine, corynebacterium parvum, levamisole, polysaccharide-K, procodazol, and the like.

In addition, L-asparaginase, aceglatone, procarbazine hydrochloride, protoporphyrin-cobalt complex, mercury-hematoporphyrin sodium salt, topoisomerase I inhibitors (e.g., irinotecan, topotecan etc.), topoisomerase II inhibitors (e.g., sobuzoxane etc.), differentiation promoter (e.g., retinoid, vitamin D etc.), inhibitor of proliferation factor (e.g., suramin etc.), antibodies (e.g., herceptin etc.), angiogenesis inhibitors, α-blocker (e.g., tamsulosin hydrochloride etc.), tyrosine kinase inhibitors, and the like can be used.

Together with the chemotherapy including administration of the compound of the present invention, therapies other than chemotherapies, such as an operation including orchiectomy, thermotherapy, radiotherapy and the like can be conducted.

Particularly, the compound of the present invention can remove androgens or estrogens in blood more effectively by using a LHRH modulator such as LHRH agonist (e.g., goserelin acetate, buserelin, leuprorelin etc.) and LHRH antagonist (e.g., ganirelix, cetrorelix, abarelix etc.) in combination.

The compound of the present invention has high selectivity to steroid $C_{17,20}$-lyase, and reduces androgen concentration without affecting drug metabolizing enzymes such as CYP3A4 and the like. Therefore, the compound becomes a useful androgen and estrogen reducer that can be used safely as a combination drug.

Examples of the pharmaceutically acceptable carrier include various organic or inorganic carriers conventionally used as materials for pharmaceuticals, which are added as appropriate in suitable amounts as exipients, lubricants, binders, disintegrators, thickeners for solid preparations; solvents, dispersants, solubilizing agents, suspending agents, isotonic agents, buffer agents, soothing agents for liquid preparations, and the like. Where necessary, additives such as preservatives, antioxidants, coloring agents, sweetening agents etc. can be used. Examples of preferable excipients include lactose, saccharose, D-mannitol, starch, crystalline cellulose, light anhydrous silicic acid and the like. Examples of preferable lubricants include magnesium stearate, calcium stearate, talc, colloidal silica, and the like. Examples of preferable binders include crystalline cellulose, saccharose, D-mannitol, dextrin, hydroxypropylcellulose, hydroxypropyl methylcellulose, polyvinylpyrrolidone, and the like. Examples of preferable disintegrators include starch, carboxymethylcellulose, calcium carboxymethylcellulose, sodium croscarmellose, sodium carboxymethyl starch, and the like. Examples of preferable thickener include natural rubbers, cellulose derivatives, acrylate polymers, and the like. Examples of preferable solvent include water for injection, alcohol, propylene glycol, Macrogol, sesame oil, corn oil, and the like.

Examples of preferable dispersant include Tween 80, HCO 60, polyethylene glycol, carboxymethylcellulose, sodium alginate, and the like. Examples of preferable solubilizing agent include polyethylene glycol, propylene glycol, D-mannitol, benzyl benzoate, ethanol, trisaminomethane, cholesterol, triethanolamine, sodium carbonate, sodium citrate, and the like. Examples of preferable suspending agents include surfactants, such as stearyl triethanolamine, sodium laurylsulfate, laurylaminopropionic acid, lecithin, benzalkonium chloride, benzethonium chloride, glycerin monostearate etc.; hydrophilic polymer such as polyvinyl alcohol, polyvinylpyrrolidone, sodium carboxymethylcellulose, methylcellulose, hydroxymethylcellulose, hydroxyethylcellulose, hydroxypropylcellulose etc.; and the like. Examples of preferable isotonic agents include sodium chloride, glycerin, D-mannitol and the like. Examples of preferable buffer agents include buffer solutions such as phosphate, acetate, carbonate, citrate etc., and the like. Examples of preferable soothing agents include benzyl alcohol, and the like. Examples of preferable preservatives include paraoxybenzoic acid ester, chlorobutanol, benzyl alcohol, phenethyl alcohol, dehydroacetic acid, sorbic acid, and the like. Examples of preferable antioxidants include sulfite, ascorbic acid, and the like.

The pharmaceutical composition of the present invention can be manufactured by a conventional method. The ratio of compound of the present invention contained in a pharmaceutical preparation is usually 0.1 to 100% (w/w). Specific examples are shown below.

(1) Tablets, Powder, Granules, Capsules:

These can be produced by adding, for example, exipients, disintegrators, binders, lubricants etc. to the compound of the present invention, compression forming the mixture and, where necessary, coating for masking of taste, enteric or sustained release.

(2) Injection:

This can be produced by preparing the compound of the present invention into an aqueous injection together with, for example, dispersants, preservatives, isotonic agents etc., or into an oily injection by dissolving, suspending or emulsifying the compound in a vegetable oil such as olive oil, sesame oil, cotton seed oil, corn oil etc., or propylene glycol etc.

(3) Suppository:

This can be produced by preparing the compound of the present invention into an oily or aqueous solid, semisolid or liquid composition. Examples of oily base used for the composition include glyceride of higher fatty acid (e.g., cacao butter, witepsols etc.), middle fatty acid (e.g., miglyols etc.), vegetable oils (e.g., sesame oil, soybean oil, cotton seed oil etc.) and the like. Examples of aqueous gel base include natural rubbers, cellulose derivative, vinyl polymer, acrylate polymer, and the like.

The content of the compound of the present invention admixed in these preparations is usually 0.01 to 50%, though subject to change depending upon the kind of preparations.

While the amount of the compound of the present invention to be contained in the above-mentioned pharmaceutical preparation varies depending upon the compound selected, the kind of animal to be the administration target, administration frequency and the like, the compound proves effective over a broad range. The daily dose of the pharmaceutical preparation of the present invention as an effective amount of the compound of the present invention, for example, in the case of oral administration to an adult patient with a solid tumor (e.g., patient with prostate cancer) is generally about 0.001 to about 500 mg/kg body weight, preferably about 0.1 to about 40 mg/kg body weight, more preferably about 0.5 to about 20 mg/kg body weight. When the compound is parenterally administered or administered concurrently with a different anticancer agent, the dose generally becomes less than those mentioned above. The amount of the compound actually administered is determined according to the selection of compound, dosage form of each preparation, age, body weight and sex of patient, degree of disease, administration route, period and intervals of administration and the like, which can be varied according to the judgement of a doctor.

The administration route of the aforementioned pharmaceutical preparation is free of any particular limitaion by various conditions. The preparation can be administered, for example, orally or parenterally. Examples of the parenteral used here include intravenous, intramuscular, subcutaneous, intranasal, intradermal, instillation, intracerebral, intrarectal, intravaginal and intraperitoneal administrations, and the like.

The above-mentioned administration term and administration interval vary depending upon various conditions and determined any time by judgement of a doctor. Divided administration, consecutive administration, intermittent administration, high dose short period administration, repeat administration and the like can be employed. For oral administration, for example, the dose is desirably given once a day or divided into several portions (especially two or three doses a day) and administered. Administration of a sustained release preparation or intravenous drip infusion over a long time is also possible.

EXAMPLES

The present invention is explained in more detail by referring to the following Examples, Preparation Examples and Experimental Examples. These examples are mere embodiments and do not limit the present invention in any way. They may be modified within the range that does not deviate from the scope of the present invention. The abbreviations in Examples mean the following.

s: singlet, d: doublet, t: triplet, q: quartet, dd: double doublet, dt: double triplet, m: multiplet, br: broad, J: coupling constant, room temperature: 0–30° C., DMF: dimethylformamide, THF: tetrahydrofuran, Tr: trityl, TBS: tert-butyldimethylsilyl.

Reference Example 1

Production of 1-(6-tert-butyldimethylsilyloxy-2-naphthyl)-2-methyl-1-(1-trityl-1H-imidazol-4-yl)-1-propanol

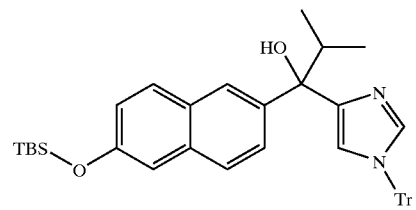

6-Bromo-2-tert-butyldimethylsilyloxynaphthalene (60.0 g) was dissolved in THF (600 mL) and the solution was cooled to −70° C. A solution (1.6 M: 111 mL) of n-butyllithium in hexane was slowly added dropwise and the mixture was stirred for 30 min. Then a solution (200 mL) of isopropyl(1-trityl-1H-imidazol-4-yl)ketone (52.1 g) in THF was added dropwise. The mixture was stirred at −70° C. for 30 min. and water was added to stop the reaction. The organic layer was separated and the aqueous layer was extracted with ethyl acetate. The combined organic layers were washed with water and saturated brine, dried and concentrated. The residue was recrystallized from ethyl acetate-hexane to give the title compound (79.5 g) as a colorless powder.

$^1$H-NMR (CDCl$_3$) δ: 0.23 (6H, s), 0.75 (3H, d, J=6.8 Hz), 0.95 (3H, d, J=6.6 Hz), 1.02 (9H, s), 2.45–2.59 (1H, m), 3.66 (1H, s), 6.80 (1H, d, J=1.4 Hz), 7.04 (1H, dd, J=2.4, 8.8 Hz), 7.11–7.16 (6H, m), 7.30–7.34 (11H, m), 7.49 (1H, dd, J=1.6, 8.6 Hz), 7.60 (1H, d, J=8.6 Hz), 7.68 (1H, d, J=8.8 Hz), 7.94 (1H, s). IR (KBr): 3158, 2955, 2930, 1601, 1493, 1480, 1445, 1260, 843 cm$^{-1}$.

Reference Example 2

Production of 6-(1-hydroxy-2-methyl-1-(1-trityl-1H-imidazol-4-yl)propyl)-2-naphthol

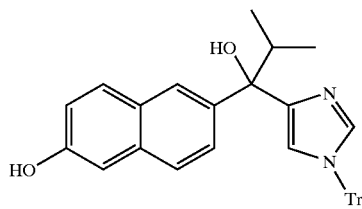

1-(6-tert-Butyldimethylsilyloxy-2-naphthyl)-2-methyl-1-(1-trityl-1H-imidazol-4-yl)-1-propanol (35.0 g) was dissolved in THF (100 mL) and cooled to 0° C. A solution (1 M: 100 mL) of tetrabutylammonium fluoride in THF was added dropwise. The mixture was stirred at room temperature for 1 hr., and the solvent was evaporated and water was added to the residue. The resulting precipitate was collected by filtration, washed with ether and water and dried to give the title compound (28.3 g) as a colorless powder.

$^1$H-NMR (CDCl$_3$+CD$_3$OD) δ: 0.76 (3H, d, J=6.8 Hz), 0.95 (3H, d, J=6.6 Hz), 2.27–2.71 (1H, m), 6.86 (1H, d, J=1.4 Hz), 7.05–7.17 (7H, m), 7.31–7.38 (11H, m), 7.48 (1H, dd, J=1.8, 8.6 Hz), 7.58 (1H, d, J=8.8 Hz), 7.67 (1H, d, J=8.6 Hz), 7.85 (1H, s). IR (KBr): 3598, 2965, 1603, 1445, 1250, 1223, 1171, 760, 748, 702 cm$^{-1}$.

Reference Example 3

Production of 6-[1-hydroxy-2-methyl-1-(1-trityl-1H-imidazol-4-yl)propyl]-2-naphthyl trifluoromethanesulfonate

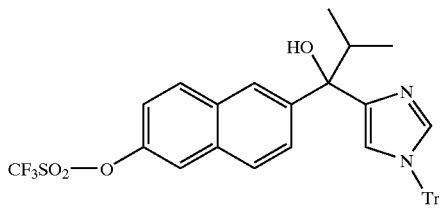

6-(1-Hydroxy-2-methyl-1-(1-trityl-1H-imidazol-4-yl)propyl)-2-naphthol (27.0 g) was dissolved in pyridine (200 mL) and cooled to 0° C. Trifluoromethanesulfonic anhydride (9.1 mL) was slowly added dropwise. The mixture was stirred under ice-cooling for 1 hr., diluted with water and extracted with ethyl acetate. The organic layer was washed with saturated brine, dried and concentrated. The residue was purified by column chromatography (eluent, hexane:ethyl acetate=1:1) and recrystallized from isopropyl ether to give the title compound (29.6 g) as a colorless powder.

$^1$H-NMR (CDCl$_3$) δ: 0.73 (3H, d, J=6.6 Hz), 0.96 (3H, d, J=6.6 Hz), 2.47–2.60 (1H, m), 3.72 (1H, br s), 6.82 (1H, d, J=1.4 Hz), 7.10–7.17 (6H, m), 7.30–7.35 (11H, m), 7.65 (1H, dd, J=1.7, 8.6 Hz), 7.70 (1H, d, J=2.6 Hz), 7.77 (1H, d, J=8.6 Hz), 7.88 (1H, d, J=9.0 Hz), 8.11 (1H, s). IR (KBr): 3164, 2965, 1431, 1412, 1242, 1211, 1142, 909, 897, 748, 702 cm$^{-1}$.

Reference Example 4

Production of methyl 6-[1-hydroxy-2-methyl-1-(1-trityl-1H-imidazol-4-yl)propyl]-2-naphthoate

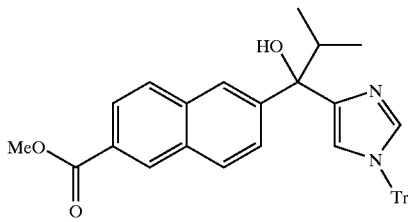

6-[1-Hydroxy-2-methyl-1-(1-trityl-1H-imidazol-4-yl)propyl]-2-naphthyl trifluoromethanesulfonate (7.0 g), (1,1'-bis(diphenylphosphino)ferrocene)dichloropalladium dichloromethane complex (441 mg) and triethylamine (2.98 mL) were dissolved in a DMF-methanol (1:1) mixed solution (80 mL) and the mixture was stirred under a carbon monoxide atmosphere. under atmospheric pressure at 60° C. for 10 hrs. The solvent was evaporated and the residue was diluted with water and extracted with ethyl acetate. The organic layer was washed with water and saturated brine, dried and concentrated. The residue was purified by column chromatography (eluent, hexane:THF=1:2) to give the title compound (5.65 g) as a pale-yellow powder.

$^1$H-NMR (CDCl$_3$) δ: 0.74 (3H, d, J=7.0 Hz), 0.97 (3H, d, J=6.6 Hz), 2.47–2.61 (1H, m), 3.75 (1H, s), 3.97 (3H, s), 6.82 (1H, d, J=1.2 Hz), 7.10–7.16 (6H, m), 7.29–7.35 (10H, m), 7.62 (1H, dd, J=1.8, 8.6 Hz), 7.81 (1H, d, J=3.2 Hz), 7.85 (1H, d, J=3.2 Hz), 8.02 (1H, dd, J=1.8 Hz, 8.6 Hz), 8.07 (1H, s), 8.55 (1H, s). IR (KBr): 3542, 2965, 1707, 1441, 1279, 1231, 747, 700 cm$^{-1}$.

Reference Example 5

Production of 1-(6-tert-butyldimethylsilyloxy-5-methyl-2-naphthyl)-2-methyl-1-(1-trityl-1H-imidazol-4-yl)-1-propanol

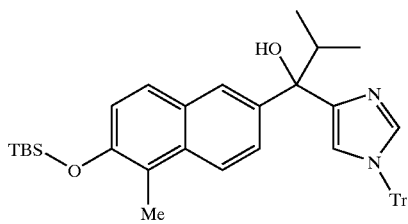

By a similar reaction as in Reference Example 1 using 6-bromo-2-tert-butyldimethylsilyloxy-1-methylnaphthalene (17.0 g), the title compound (21.6 g) was obtained as a colorless powder.

¹H-NMR (CDCl₃) δ: 0.22 (6H, s), 0.75 (3H, d, J=6.6 Hz), 0.95 (3H, d, J=6.6 Hz), 1.05 (9H, s), 2.50 (3H, s), 3.64 (1H, s), 6.80 (1H, d, J=1.2 Hz), 7.03 (1H, d, J=8.8 Hz), 7.10–7.16 (6H, m), 7.28–7.34 (10H, m), 7.55 (1H, d, J=8.8 Hz), 7.56 (1H, dd, J=1.8, 9.0 Hz), 7.81 (1H, d, J=9.0 Hz), 7.92 (1H, d, J=1.8 Hz). IR (KBr): 3200, 2961, 1472, 1242, 839, 702 cm⁻¹.

Reference Example 6

Production of 6-[1-hydroxy-2-methyl-1-(1-trityl-1H-imidazol-4-yl)propyl]-1-methyl-2-naphthol

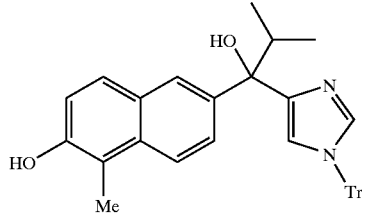

By a similar reaction as in Reference Example 2 using 1-(6-tert-butyldimethylsilyloxy-5-methyl-2-naphthyl)-2-methyl-1-(1-trityl-1H-imidazol-4-yl)-1-propanol (20 g), the title compound (15.6 g) was obtained as a colorless powder.

¹H-NMR (CDCl₃) δ: 0.69 (3H, d, J=6.6 Hz), 1.03 (3H, d, J=6.6 Hz), 2.30–2.43 (1H, m), 2.43 (3H, s), 3.89 (1H, s), 6.04 (1H, d, J=8.8 Hz), 6.49 (1H, d, J=8.8 Hz), 6.85–6.93 (2H, m), 7.21–7.25 (6H, m), 7.37–7.48 (10H, m), 7.55 (1H, d, J=8.8 Hz), 7.56 (1H, d, J=1.0 Hz). IR (KBr): 3511, 2976, 1485, 1445, 1348, 1169, 1001, 758, 702 cm⁻¹.

Reference Example 7

Production of 6-[1-hydroxy-2-methyl-1-(1-trityl-1H-imidazol-4-yl)propyl]-1-methyl-2-naphthyl trifluoromethanesulfonate

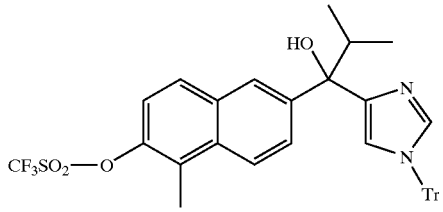

By a similar reaction as in Reference Example 3 using 6-(1-hydroxy-2-methyl-1-(1-trityl-1H-imidazol-4-yl)propyl-1-methyl-2-naphthol (14 g), the title compound (10.7 g) was obtained as a colorless powder.

¹H-NMR (CDCl₃) δ: 0.73 (3H, d, J=6.6 Hz), 0.96 (3H, d, J=6.6 Hz), 2.48–2.63 (1H, m), 2.67 (3H, s), 3.70 (1H, s), 6.82 (1H, d, J=1.4 Hz), 7.10–7.16 (6H, m), 7.29–7.35 (11H, m), 7.69–7.74 (2H, m), 7.95 (1H, d, J=8.8 Hz), 8.07 (1H, d, J=1.8 Hz). IR (KBr): 3208, 2973, 1408, 1219, 1140, 897, 702 cm⁻¹.

Reference Example 8

Production of methyl 6-(1-hydroxy-2-methyl-1-(1-trityl-1H-imidazol-4-yl)propyl)-1-methyl-2-naphthoate

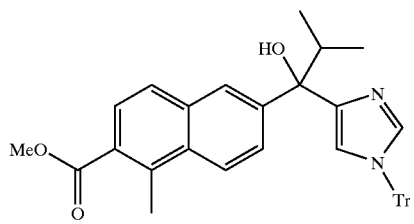

By a similar reaction as in Reference Example 4 using 6-(1-hydroxy-2-methyl-1-(1-trityl-1H-imidazol-4-yl)propyl-1-methyl-2-naphthyl trifluoromethanesulfonate (6.0 g), the title compound (4.2 g) was obtained as a colorless powder.

¹H-NMR (CDCl₃) δ: 0.74 (3H, d, J=7.0 Hz), 0.76 (3H, d, J=6.0 Hz), 2.48–2.62 (1H, m), 2.91 (3H, s), 3.74 (1H, s), 3.94 (3H, s), 6.82 (1H, d, J=1.4 Hz), 7.10–7.15 (6H, m), 7.30–7.34 (10H, m), 7.64–7.70 (2H, m), 7.80 (1H, d, J=8.8 Hz), 8.02 (1H, d, J=1.4 Hz), 8.08 (1H, d, J=9.2 Hz). IR (KBr): 3162, 2969, 1719, 1445, 1240, 1173, 747, 700 cm⁻¹.

Reference Example 9

Production of 1-(6-tert-butyldimethylsilyloxy-7-methyl-2-naphthyl)-2-methyl-1-(1-trityl-1H-imidazol-4-yl)-1-propanol

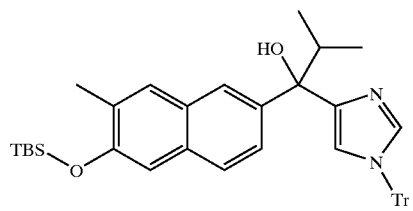

By a similar reaction as in Reference Example 1 using 6-bromo-2-tert-butyldimethylsilyloxy-3-methylnaphthalene (14.5 g), the title compound (19.2 g) was obtained as a pale-yellow powder.

¹H-NMR (CDCl₃) δ: 0.27 (6H, s), 0.75 (3H, d, J=6.6 Hz), 0.94 (3H, d, J=6.6 Hz), 1.05 (9H, s), 2.35 (3H, s), 2.45–2.58 (1H, m), 3.67 (1H, s), 6.80 (1H, d, J=1.2 Hz), 7.06 (1H, s), 7.11–7.15 (6H, m), 7.30–7.33 (10H, m), 7.44 (1H, dd, J=1.8, 8.6 Hz), 7.53–7.57 (2H, m), 7.86 (1H, s). IR (KBr): 3198, 1472, 1445, 1250, 1163, 1124, 914, 700 cm⁻¹.

Reference Example 10

Production of 6-(1-hydroxy-2-methyl-1-(1-trityl-1H-imidazol-4-yl)propyl)-3-methyl-2-naphthol

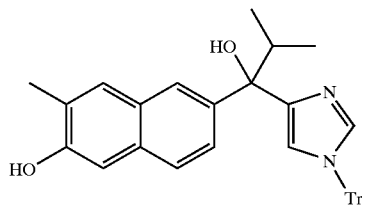

By a similar reaction as in Reference Example 2 using 1-(6-tert-butyldimethylsilyloxy-7-methyl-2-naphthyl)-2-methyl-1-(1-trityl-1H-imidazol-4-yl)-1-propanol (18.5 g), the title compound (14.9 g) was obtained as a colorless powder.

$^1$H-NMR (DMSO-d$_6$) δ: 0.61 (3H, d, J=6.8 Hz), 0.71 (3H, d, J=6.6 Hz), 2.27 (3H, s), 2.54–2.64 (1H, m), 5.04 (1H, s), 6.83 (1H, d, J=1.4 Hz), 7.03–7.08 (6H, m), 7.29 (1H, d, J=1.4 Hz), 7.33–7.41 (10H, m), 7.45–7.50 (2H, m), 7.69 (1H, dd, J=1.4, 8.8 Hz), 7.84 (1H, s). IR (KBr): 3603, 2966, 1670, 1447, 1244, 1159, 760, 748, 704 cm$^{-1}$.

Reference Example 11

Production of 6-[1-hydroxy-2-methyl-1-(1-trityl-1H-imidazol-4-yl)propyl]-3-methyl-2-naphthyl trifluoromethanesulfonate

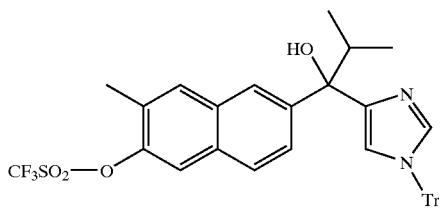

By a similar reaction as in Reference Example 3 using 6-(1-hydroxy-2-methyl-1-(1-trityl-1H-imidazol-4-yl)propyl)-3-methyl-2-naphthol (14.0 g), the title compound (12.9 g) was obtained as a yellow powder.

$^1$H-NMR (CDCl$_3$) δ: 0.72 (3H, d, J=7.0 Hz), 0.96 (3H, d, J=7.0 Hz), 2.46–2.59 (1H, m), 2.51 (3H, s), 3.72 (1H, s), 6.80 (1H, d, J=1.6 Hz), 7.09–7.16 (6H, m), 7.29–7.36 (10H, m), 7.56 (1H, dd, J=1.8, 8.6 Hz), 7.67–7.73 (3H, m), 8.02 (1H, s). IR (KBr): 3219, 2966, 1408, 1215, 1140, 1055, 895, 748, 700 cm$^{-1}$.

Reference Example 12

Production of methyl 6-[1-hydroxy-2-methyl-1-(1-trityl-1H-imidazol-4-yl)propyl]-3-methyl-2-naphthoate

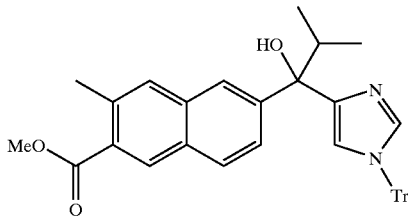

By a similar reaction as in Reference Example 4 using 6-[1-hydroxy-2-methyl-1-(1-trityl-1H-imidazol-4-yl)propyl]-3-methyl-2-naphthyl trifluoromethanesulfonate (9.0 g), the title compound (6.8 g) was obtained as a pale-brown powder.

$^1$H-NMR (CDCl$_3$) δ: 0.73 (3H, d, J=6.8 Hz), 0.95 (3H, d, J=6.6 Hz), 2.45–2.59 (1H, m), 2.71 (3H, s), 3.73 (1H, s), 3.94 (3H, S), 6.80 (1H, d, J=1.6 Hz), 7.10–7.16 (6H, m), 7.29–7.36 (10H, m), 7.54 (1H, dd, J=1.6, 8.6 Hz), 7.59 (1H, d, J=8.6 Hz), 7.96 (1H, s), 8.44 (1H, s). IR (KBr): 3223, 2968, 1724, 1445, 1283, 1267, 748, 700 cm$^{-1}$.

Reference Example 13

Production of methyl 1-bromomethyl-6-[1-hydroxy-2-methyl-1-(1-trityl-1H-imidazol-4-yl)propyl]-2-naphthoate

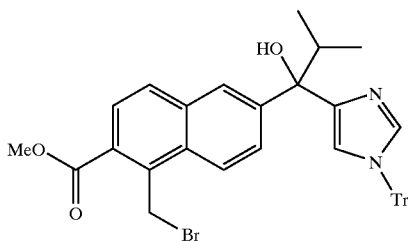

Methyl 6-[1-hydroxy-2-methyl-1-(1-trityl-1H-imidazol-4-yl)propyl]-1-methyl-2-naphthoate (34.61 g) was suspended in carbon tetrachloride (0.8 L) and N-bromosuccinimide (12.28 g) and 2,2'-azobisisobutyronitrile (0.99 g) were added. The reaction mixture was heated under reflux for 21 hrs., and the solvent was evaporated. The residue was diluted with saturated aqueous sodium hydrogen carbonate and extracted twice with ethyl acetate-THF (1:1). The organic layers were combined, washed with saturated brine, dried over anhydrous magnesium sulfate and concentrated. The obtained residue was purified by column chromatography (carrier;silica gel, developing solvent; ethyl acetate) to give a mixture of the title compound and the starting material (title compound:starting material=about 7:1, 23.10 g) as brown crystals.

$^1$H-NMR (CDCl$_3$) δ: 0.74 (3H, d, J=6.8 Hz), 0.98 (3H, d, J=6.8 Hz), 2.55 (1H, septet, J=6.8 Hz), 3.78 (1H, s), 3.99 (3H, s), 5.43 (1H, d, J=9.8 Hz), 5.47 (1H, d, J=9.8 Hz), 6.82 (1H, d, J=1.4 Hz), 7.10–7.35 (16H, m), 7.72 (1H, dd, J=8.8, 1.8 Hz), 7.81 (1H, d, J=8.8 Hz), 7.92 (1H, d, J=8.8 Hz), 8.10 (1H, d, J=1.8 Hz), 8.18 (1H, d, J=8.8 Hz). IR (KBr): 1725, 1238, 702 cm$^{-1}$.

Reference Example 14

Production of methyl 3-bromomethyl-6-[1-hydroxy-2-methyl-1-(1-trityl-1H-imidazol-4-yl)propyl]-2-naphthoate

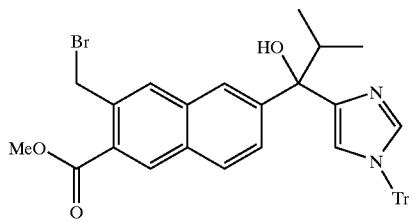

Methyl 6-[1-hydroxy-2-methyl-1-(1-trityl-1H-imidazol-4-yl)propyl]-3-methyl-2-naphthoate (5.93 g) was suspended in carbon tetrachloride (150 ml) and N-bromosuccinimide (2.01 g) and 2,2'-azobisisobutyronitrile (0.17 g) were added. The reaction mixture was heated under reflux for 4 hrs. and the solvent was concentrated. The residue was diluted with saturated aqueous sodium hydrogen carbonate and extracted with ethyl acetate. The organic layer was washed with saturated brine, dried over anhydrous magnesium sulfate and concentrated to give a crude title compound (6.70 g) as a brown amorphous solid.

$^1$H-NMR (CDCl$_3$) δ: 0.73 (3H, d, J=6.6 Hz), 0.97 (3H, d, J=6.6 Hz), 2.53 (1H, septet, J=6.6 Hz), 3.74 (1H, s), 4.00 (3H, s), 5.12 (1H, d, J=10.4 Hz), 5.15 (1H, d, J=10.4 Hz), 6.81 (1H, d, J=1.0 Hz), 7.09–7.38 (16H, m), 7.65 (1H, dd, J=8.4, 1.6 Hz), 7.78–7.84 (2H, m), 8.02 (1H, s), 8.50 (1H, s).

Reference Example 15

Production of (6-tert-butyldimethylsilyloxy-5-methyl-2-naphthyl)(1-trityl-1H-imidazol-4-yl)methanone

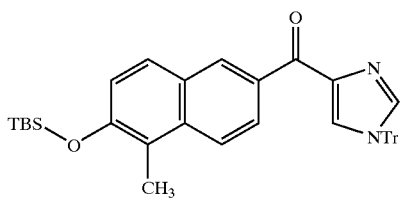

6-Bromo-2-tert-butyldimethylsilyloxy-1-methylnaphthalene (35.1 g) was dissolved in THF (350 mL) and the solution was cooled to −70° C. A solution (1.6 M: 82 mL) of n-butyllithium in hexane was slowly added dropwise and the mixture was stirred for 1 hr. Then, a solution (300 mL) of 4-formyl-1-trityl-1H-imidazole (30.5 g) in THF was added dropwise. After stirring at −70° C. for 30 min., the reaction was stopped by adding 20% aqueous ammonium chloride. The organic layer was separated and the aqueous layer was extracted with ethyl acetate. The combined organic layers were washed with saturated brine, dried over anhydrous magnesium sulfate and concentrated to give crude (6-tert-butyldimethylsilyloxy-5-methyl-2-naphthyl)(1-trityl-1H-imidazol-4-yl)methanol as an amorphous solid.

This amorphous solid was dissolved in dichloromethane (500 mL) and manganese dioxide (80 g) was added. The mixture was stirred at room temperature for 50 hrs. The insoluble material was filtered off and the filtrate was concentrated. The obtained residue was purified by column chromatography (carrier: silica gel, developing solvent:hexane-ethyl acetate, 8:1→4:1). The obtained crystals were washed with diisopropyl ether and dried to give the title compound (30.5 g) as colorless crystals.

$^1$H-NMR (CDCl$_3$) δ: 0.25 (6H, s), 1.06 (9H, s), 2.53 (3H, s), 7.07–7.40 (16H, m), 7.58 (1H, d, J=1.4 Hz), 7.69–7.76 (2H, m), 7.96 (1H, d, J=9.2 Hz), 8.21 (1H, dd, J=9.2, 1.4 H), 8.91 (1H, s). IR (KBr): 1470, 1181, 922, 843, 700 cm$^{-1}$.

Reference Example 16

Production of 1-methyl-6-[(1-trityl-1H-imidazol-4-yl)carbonyl]-2-naphthol

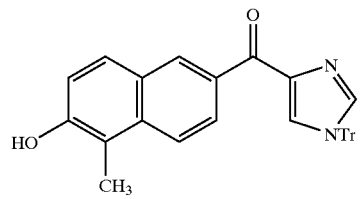

(6-tert-Butyldimethylsilyloxy-5-methyl-2-naphthyl)(1-trityl-1H-imidazol-4-yl)methanone (30.0 g) was dissolved in THF (200 mL) and tetrabutylammonium fluoride (14.9 g) was added. The mixture was stirred at room temperature for 18 hrs. and the solvent was evaporated. Water was added to the residue and the mixture was extracted with ethyl acetate. The extracted layer was washed with saturated brine, dried over anhydrous magnesium sulfate and concentrated. The residue was washed with diisopropyl ether and dried to give the title compound (22.4 g) as pale-orange crystals.

$^1$H-NMR (CDCl$_3$+CD$_3$OD) δ: 2.49 (3H, s), 7.09 (1H, d, J=8.8 Hz), 7.15–7.22 (6H, m), 7.34–7.40 (9H, m), 7.58–7.62 (2H, m), 7.70 (1H, s), 7.90 (1H, d, J=5.2 Hz), 8.12 (1H, dd, J=8.8, 1.8 Hz), 8.66 (1H, d, J=1.4 Hz). IR (KBr): 3380, 1611, 1310, 1186, 748, 702 cm$^{-1}$.

Reference Example 17

Production of 1-methyl-6-[(1-trityl-1H-imidazol-4-yl)carbonyl]-2-naphthyl trifluoromethanesulfonate

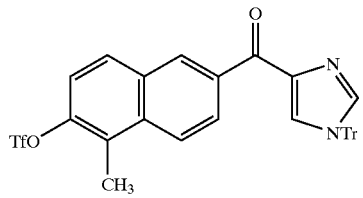

1-Methyl-6-[(1-trityl-1H-imidazol-4-yl)carbonyl]-2-naphthol (22.3 g) was dissolved in pyridine (100 mL) and cooled to 0° C. Then, trifluoromethanesulfonic anhydride (9.3 mL) was slowly added dropwise. The mixture was stirred under ice-cooling for 30 min. and then at room temperature for 1 hr., the reaction mixture was diluted with water (1.0 L) and the supernatant was removed. The residue was dissolved in ethyl acetate, washed successively with 10% citric acid and saturated aqueous sodium hydrogen carbonate and dried over magnesium sulfate. The solvent was evaporated, and the residue was suspended in hexane and filtrated to give the title compound (26.9 g) as colorless crystals.

¹H-NMR (CDCl₃) δ: 2.72 (3H, s), 7.15–7.43 (16H, m), 7.58 (1H, d, J=1.4 Hz), 7.83 (1H, d, J=1.4 Hz), 7.91 (1H, d, J=9.2 Hz), 8.02 (1H, d, J=8.8 Hz), 8.41 (1H, dd, J=9.2, 1.8 Hz), 9.05 (1H, d, J=1.8 Hz). IR (KBr): 1640, 1512, 1399, 1215, 1171, 903, 750, 702 cm⁻¹.

Reference Example 18

Production of methyl 1-methyl-6-[(1-trityl-1H-imidazol-4-yl)carbonyl]-2-naphthoate

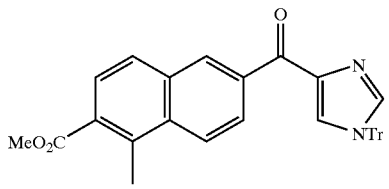

A mixture of 1-methyl-6-[(1-trityl-1H-imidazol-4-yl)carbonyl]-2-naphthyl trifluoromethanesulfonate (26.8 g), triethylamine (15.7 mL), methanol (50 mL), palladium acetate (0.61 g), 1,1'-bis(diphenylphosphino)ferrocene (1.50 g) and DMF (150 mL) was stirred under a carbon monooxide atmosphere with heating at 70° C. for 16 hrs. The reaction mixture was cooled and diluted with water (1.6 L). The precipitate was collected by filtration and purified by column chromatography (carrier: silica gel, developing solvent: ethyl acetate). The obtained crystal was washed with diisopropyl ether and dried to give the title compound (20.9 g) as-colorless crystals.

¹H-NMR (CDCl₃) δ: 2.93 (3H, s), 3.97 (3H,s), 7.15–7.40 (15H, m), 7.58 (1H, s), 7.80–7.84 (3H, m), 8.24 (1H, d, J=8.8 Hz), 8.34 (1H, dd, J=8.8, 1.6 Hz), 8.95 (1H, d, J=1.6 Hz). IR (KBr): 1721, 1632, 1231, 1184, 750, 702 cm⁻¹.

Reference Example 19

Production of methyl 1-bromomethyl-6-[(1-trityl-1H-imidazol-4-yl)carbonyl]-2-naphthoate

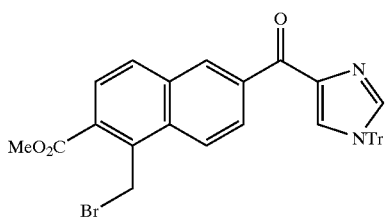

Methyl 1-methyl-6-[(1-trityl-1H-imidazol-4-yl)carbonyl]-2-naphthoate (20.7 g) was suspended in carbon tetrachloride (400 mL) and N-bromosuccinimide (7.5 g) and 2,2'-azobisisobutyronitrile (0.58 g) were added. The reaction mixture was heated under reflux for 5 hrs. and concentrated. The residue was diluted with saturated aqueous sodium hydrogen carbonate and extracted twice with ethyl acetate. The organic layers were combined, washed with saturated brine, dried over anhydrous magnesium sulfate and concentrated to give a crude title compound (25.7 g) as a brown amorphous solid.

¹H-NMR (CDCl₃) δ: 4.02 (3H, s), 5.44 (2H,s), 7.13–7.40 (15H, m), 7.59 (1H, d, J=1.0 Hz), 7.83 (1H, d, J=1.8 Hz), 7.95 (1H, d, J=8.8 Hz), 8.01 (1H, d, J=8.8 Hz), 8.36 (1H, d, J=8.8 Hz), 8.45 (1H, dd, J=8.8, 1.8 Hz), 9.01 (1H, d, J=1.0 Hz). IR (KBr): 1721, 1248, 702 cm⁻¹.

Reference Example 20

Production of 2-methyl-7-[(1-trityl-1H-imidazol-4-yl)carbonyl]-1,2-dihydro-3H-benzo[e]isoindol-3one

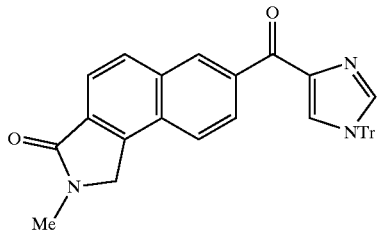

Methyl 1-bromomethyl-6-[(1-trityl-1H-imidazol-4-yl)carbonyl]-2-naphthoate (14.0 g) was dissolved in THF (120 mL), and 40% methylamine methanol solution (60 mL) was added. The reaction mixture was stirred at room temperature for 20 hrs. and the solvent was evaporated. The residue was purified by column chromatography (carrier: silica gel, developing solvent: dichloromethane-methanol=40:1) and crystallized from ethyl acetate-diethyl ether to give the title compound (5.5 g) as colorless crystals.

¹H-NMR (CDCl₃) δ: 3.30 (3H, s), 4.75 (2H, s), 7.16–7.41 (15H, m), 7.59 (1H, s), 7.83–7.93 (3H, m), 8.04 (1H, d, J=8.8 Hz), 8.38 (1H, d, J=8.8 Hz), 9.10 (1H, s). IR (KBr): 1698, 1630, 1518, 1179, 760, 747, 706 cm⁻¹.

Reference Example 21

Production of 6-bromo-N,N-diisopropyl-2-naphthamide

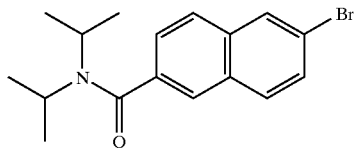

A suspension of 6-bromo-2-naphthoic acid (100 g), thionyl chloride (37.7 mL) and DMF (0.5 mL) in THF (1000 mL) was stirred with heating at 60° C. for 90 min. The mixture was cooled to room temperature and the solvent was evaporated under reduced pressure. The obtained solid was dissolved in toluene and the solvent was evaporated to give a pale-yellow powder of 6-bromo-2-naphthoyl chloride.

To a solution (800 mL) of diisopropylamine (112 mL) and triethylamine (112 mL) in THF was added dropwise a solution (400 mL) of 6-bromo-2-naphthoyl chloride in THF under ice-cooling. The mixture was stirred at room temperature for 1 hr. A half amount of the solvent was evaporated under reduced pressure, and the residue was diluted with ethyl acetate, washed successively with water, 1N aqueous sodium hydroxide solution, water and saturated brine and dried over magnesium sulfate. The solvent was evaporated and the obtained solid was washed with isopropyl ether to give the title compound (117 g) as colorless flakes.

¹H-NMR (CDCl₃) δ: 1.36 (12H, br s), 3.71 (2H, br s), 7.44 (1H, dd, J=1.2, 8.6 Hz), 7.58 (1H, dd, J=2.2, 8.8 Hz), 7.70–7.79 (3H, m), 8.01 (1H, d, J=1.2 Hz). IR (KBr): 2968, 1620, 1435, 1369, 1333, 895, 814 cm⁻¹.

Reference Example 22

Production of 6-[1-hydroxy-2-methyl-1-(1-trityl-1H-imidazol-4-yl)propyl]-N,N-diisopropyl-2-naphthamide

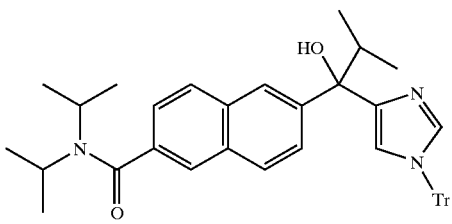

To a solution of toluene (1000 mL) containing a solution (1.6 M : 98.3 mL) of butyllithium in hexane was dropwise added a solution (250 mL) of 6-bromo-N,N-diisopropyl-2-naphthamide (50.0 g) in THF at −70° C. The mixture was stirred at the same temperature for 30 min., and a solution (200 mL) of 2-methyl-1-(1-trityl-1H-imidazol-4-yl)-1-propanone (47.5 g) in THF was added dropwise. The mixture was stirred for 20 min. Water was added and the organic layer was separated, and the aqueous layer was extracted with ethyl acetate. The combined organic layers were washed with saturated brine and dried over magnesium sulfate. The solvent was evaporated and the residue was recrystallized from isopropyl ether to give the title compound (71.1 g) as a colorless powder.

$^1$H-NMR (CDCl$_3$) δ: 0.74 (3H, d, J=7.0 Hz), 0.96 (3H, d, J=6.6 Hz), 1.37 (12H, br s), 2.47–2.61 (1H, m), 3.72 (3H, br s), 6.81 (1H, d, J=1.6 Hz), 7.10–7.17 (6H, m), 7.29–7.40 (11H, m), 7.59 (1H, dd, J=1.7, 8.5 Hz), 7.73–7.77 (2H, m), 7.81 (1H, d, J=8.4 Hz), 8.04 (1H, s). IR (KBr): 3503, 2974, 1632, 1447, 1337, 1161, 750, 702 cm$^{-1}$.

Reference Example 23

Production of 1-formyl-6-[1-hydroxy-2-methyl-1-(1-trityl-1H-imidazol-4-yl)propyl]-N,N-diisopropyl-2-naphthamide

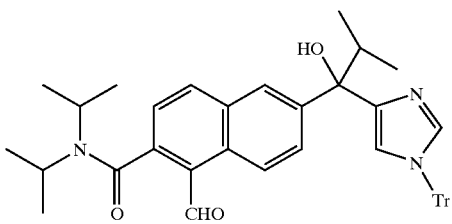

To a solution (1000 mL) of 6-[1-hydroxy-2-methyl-1-(1-trityl-1H-imidazol-4-yl)propyl]-N,N-diisopropyl-2-naphthamide (50.0 g) and N,N,N',N'-tetramethylethylenediamine (94.9 mL) in toluene was added dropwise a butyllithium hexane solution (1.6 M: 196 mL) at −70° C. After stirring at the same temperature for 2 hrs., DMF (60.9 mL) was added dropwise and mixture was stirred for 20 min. Water was added to the reaction solution and the mixture was diluted with ethyl acetate. The organic layer was washed successively with water, 10% aqueous citric acid solution, water and saturated aqueous sodium hydrogen carbonate, and dried over magnesium sulfate. The solvent was evaporated and the obtained residue was recrystallized from hexane-ethyl acetate (3:1) to give the title compound (36.0 g) as a colorless powder.

$^1$H-NMR (CDCl$_3$) δ: 0.73 (3H, d, J=7.0 Hz), 0.98 (3H, d, J=7.0 Hz), 1.10 (6H, d, J=6.6 Hz), 1.63 (6H, d, J=6.8 Hz), 2.47–2.61 (1H, m), 3.51–3.69 (2H, m), 3.79 (1H, s), 7.82 (1H, d, J=1.4 Hz), 7.09–7.16 (6H, m), 7.29–7.35 (11H, m), 7.70 (1H, dd, J=2.0, 9.2 Hz), 8.08 (1H, d, J=8.4 Hz), 8.17 (1H, d, J=1.8 Hz), 9.09 (1H, d, J=9.2 Hz), 10.57 (1H, s). IR (KBr): 3491, 2970, 1674, 1636, 760, 746, 702 cm$^{-1}$.

Reference Example 24

Production of 6-bromo-2-hydroxy-1-naphthaldehyde

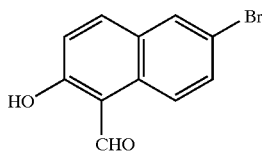

6-Bromo-2-naphthol (25.33 g) was suspended in dichloromethane (300 ml) and titanium tetrachloride (25.0 ml) was slowly added dropwise under cooling in an ice bath. 1,1-Dichloromethylmethyl ether (10.5 ml) was added dropwise to the reaction mixture and the mixture was stirred at the same temperature for 1 hr. The reaction mixture was poured into iced water and dichloromethane was added. The organic layer was separated and the aqueous layer was extracted with dichloromethane. The combined organic layers were washed successively with IN hydrochloric acid, water and saturated aqueous sodium hydrogen carbonate, dried over anhydrous magnesium sulfate and concentrated to give the title compound (28.17 g) as brown crystals.

$^1$H-NMR (CDCl$_3$) δ: 7.18 (1H, d, J=8.8 Hz), 7.69 (1H, dd, J=8.8, 2.0 Hz), 7.90 (1H, d, J=8.8 Hz), 7.96 (1H, d, J=2.0 Hz), 8.23 (1H, d, J=8.8 Hz), 10.78 (1H, s). IR (KBr): 1640, 1308, 1167, 812 cm$^{-1}$.

Reference Example 25

Production of 6-bromo-1-formyl-2-naphthyl trifluoromethanesulfonate

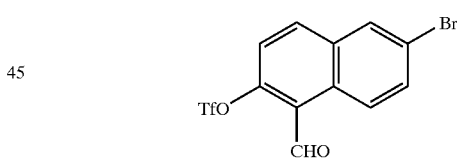

6-Bromo-2-hydroxy-1-naphthaldehyde (7.53 g) and triethylamine (9.20 ml) were dissolved in dichloromethane (150 ml) and N-phenyltrifluoromethanesulfonimide (11.25 g) was added by small portions with cooling in an ice bath. The reaction mixture was stirred at the same temperature for 1 hr. and then at room temperature for 6 hrs. The solvent was evaporated. Water was added to the residue and the mixture was extracted with ethyl acetate. The extracted layer was washed successively with 10% citric acid, water and saturated aqueous sodium hydrogen carbonate, dried over anhydrous magnesium sulfate and concentrated. The residue was purified by column chromatography (carrier: silica gel, developing solvent: dichloromethane) and the obtained crystals were washed with diisopropyl ether to give the title compound (9.15 g) as pale-brown crystals.

$^1$H-NMR (CDCl$_3$) δ: 7.52 (1H, d, J=9.2 Hz), 7.82 (1H, dd, J=9.2, 2.0 Hz), 8.10 (1H, d, J=9.2 Hz), 8.10 (1H, d, J=2.0

Hz), 9.09 (1H, d, J=9.2 Hz), 10.75 (1H, s). IR (KBr): 1694, 1422, 1215, 1132, 957, 889 cm$^{-1}$.

Reference Example 26

Production of 7-bromo-1-methoxynaphtho[1,2-c]furan-3(1H)-one

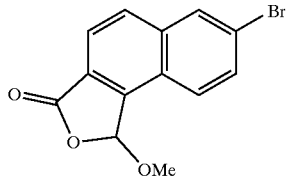

A mixture of 6-bromo-1-formyl-2-naphthyl trifluoromethanesulfonate (5.62 g), triethylamine (5.12 mL), methanol (10 mL), palladium acetate (0.20 g), 1,1'-bis(diphenylphosphino)ferrocene (0.49 g) and DMF (30 mL) was stirred under a carbon monoxide atmosphere at room temperature for 3 hrs. The reaction mixture was diluted with ethyl acetate and washed successively with 10% citric acid, water and saturated aqueous sodium hydrogen carbonate, dried over anhydrous magnesium sulfate and concentrated. The residue was purified by column chromatography (carrier: silica gel, developing solvent: hexane-ethyl acetate, 20:1–3:1) to give the title compound (1.66 g) as colorless crystals.

$^1$H-NMR (CDCl$_3$) δ: 3.67 (3H, s), 7.78 (1H, dd, J=8.8, 2.0 Hz), 7.87 (1H, d, J=8.8 Hz), 7.96 (1H, d, J=8.8 Hz), 7.98 (1H, d, J=8.8 Hz), 8.20 (1H, d, J=2.0 Hz), 6.67 (1H, s). IR (KBr): 1775, 1327, 1086, 964 cm$^{-1}$.

Reference Example 27

Production of 7-bromo-1-hydroxy-2-methyl-1,2-dihydro-3H-benzo[e]isoindol-3-one

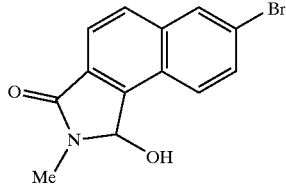

7-Bromo-1-methoxynaphtho[1,2-c]furan-3(1H)-one (1.03 g) was dissolved in THF (10 mL), and 40% methylamine methanol solution (10 mL) was added. The reaction mixture was stirred at room temperature for 1 hr., and the solvent was evaporated to give the title compound (1.03 g) as pale-yellow crystals.

$^1$H-NMR (CDCl$_3$) δ: 2.94 (1H, d, J=12.0 Hz), 3.13 (3H, s), 6.01 (1H, d, J=12.0 Hz), 7.65 (1H, d, J=8.2 Hz), 7.73 (1H, dd, J=8.8, 1.8 Hz), 7.79 (1H, d, J=8.2 Hz), 8.12 (1H, d, J=1.8 Hz), 8.16 (1H, d, J=8.8 Hz). IR (KBr): 3216, 1682, 1659, 1046, 876 cm$^{-1}$.

Reference Example 28

Production of 7-bromo-2-methyl-1,2-dihydro-3H-benzo[e]isoindol-3-one

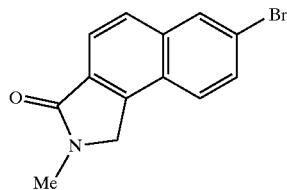

7-Bromo-1-hydroxy-2-methyl-1,2-dihydro-3H-benzo[e]isoindol-3-one (1.03 g) was dissolved in acetic acid (25 ml) and zinc (3.0 g) was added. The mixture was stirred with heating at 100° C. for 3 hrs. The reaction mixture was filtered through celite and the filtrate was concentrated. The obtained residue was diluted with saturated aqueous sodium hydrogen carbonate and extracted with ethyl acetate. The extracted layer was dried over anhydrous magnesium sulfate and concentrated. The residue was purified by column chromatography (carrier: silica gel, developing solvent: hexane-ethyl acetate, 2:1–1:1). The obtained crystals were washed with diisopropyl ether to give the title compound (0.84 g) as colorless crystals.

$^1$H-NMR (CDCl$_3$) δ: 3.28 (3H, s), 4.68 (2H, s), 7.63–7.74 (2H, m), 7.79 (1H, d, J=8.4 Hz), 7.88 (1H, d, J=8.4 Hz), 8.12 (1H, d, J=2.0 Hz). IR (KBr): 1674, 874, 812 cm$^{-1}$.

Example 1

Production of 7-[1-hydroxy-1-(1H-imidazol-4-yl)-2-methylpropyl]-1,2-dihydro-3H-benzo[e]isoindol-3-one

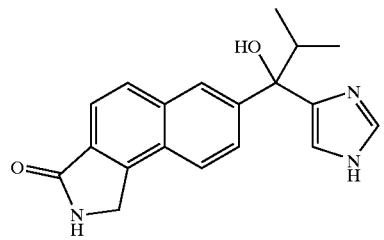

Methyl 1-bromomethyl-6-[1-hydroxy-2-methyl-1-(1-trityl-1H-imidazol-4-yl)propyl]-2-naphthoate (5.58 g) was dissolved in THF (50 ml) and the mixture was cooled in an ice bath. To this solution was added saturated ammonia methanol solution (50 ml) and the reaction mixture was stirred at room temperature for 1 hr. The solvent was evaporated and the residue was diluted with saturated aqueous sodium hydrogen carbonate. The mixture was extracted twice with a mixed solution of ethyl acetate-THF (1:1). The organic layers were combined, washed with saturated brine, dried over anhydrous magnesium sulfate and concentrated. The obtained residue was purified by column chromatography (carrier; silica gel, developing solvent; ethyl acetate:ethanol=20:1) to give 7-[1-hydroxy-2-methyl-1-(1-trityl-1H-imidazol-4-yl)propyl]-1,2-methyl-1-(1-benzo[e]isoindol-3-one as colorless crystals (1.22 g). The colorless crystals (1.17 g) were suspended in THF-methanol (1:3, 30 ml) and pyridine hydrochloride (0.29 g) was added. The reaction mixture was stirred with heating at 60° C. for 6 hrs.

and the solvent was evaporated. The residue was diluted with saturated aqueous sodium hydrogen carbonate and the mixture was extracted twice with a mixed solution of ethyl acetate-THF (1:1). The organic layers were combined, dried over anhydrous magnesium sulfate and concentrated. The obtained residue was purified by column chromatography (carrier; silica gel, developing solvent; dichloromethane:methanol=20:1) and recrystallized from ethanol-water to give the title compound as colorless crystals (0.50 g).

$^1$H-NMR (CDCl$_3$+CD$_3$OD) δ: 0.79 (3H, d, J=6.6 Hz), 1.02 (3H, d, J=6.6 Hz), 2.76 (1H, septet, J=6.6 Hz), 4.68 (2H, s), 7.04 (1H, s), 7.55 (1H, s), 7.70–7.77 (3H, m), 7.88 (1H, d, J=8.4 Hz), 8.15 (1H, s). IR (KBr): 1684, 1472, 747 cm$^{-1}$.

Example 2

Production of 7-[1-hydroxy-1-(1H-imidazol-4-yl)-2-methylpropyl]-2-methyl-1,2-dihydro-3H-benzo[e]isoindol-3-one

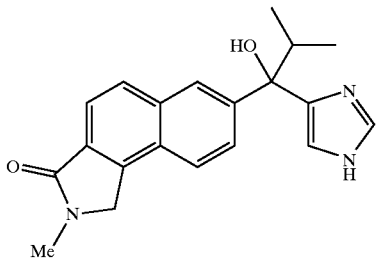

Methyl 1-bromomethyl-6-[1-hydroxy-2-methyl-1-(1-trityl-1H-imidazol-4-yl)propyl]-2-naphthoate (0.80 g) was dissolved in THF (8 ml) and 40% methylamine methanol solution (8 ml) was added. The reaction mixture was stirred at room temperature for 20 hrs. and the solvent was evaporated. The residue was suspended in ethyl acetate and filtrated to give 7-[1-hydroxy-2-methyl-1-(1-trityl-1H-imidazol-4-yl)propyl]-2-methyl-1,2-dihydro-3H-benzo[e]isoindol-3-one as a colorless solid (0.77 g). This solid was suspended in a mixed solution of THF and methanol (1:3, 20 ml) and pyridine hydrochloride (0.23 g) was added. The reaction mixture was stirred with heating at 60° C. for 6 hrs., and the solvent was evaporated. The residue was diluted with saturated aqueous sodium hydrogen carbonate and extracted twice with ethyl acetate-THF (1:1). The organic layers were combined, dried over anhydrous magnesium sulfate and concentrated. The residue was recrystallized from THF-methanol to give the title compound as colorless crystals (0.28 g).

$^1$H-NMR (CDCl$_3$+CD$_3$OD) δ: 0.80 (3H, d, J=7.0 Hz), 1.02 (3H, d, J=7.0 Hz), 2.78 (1H, septet, J=7.0 Hz), 3.29 (3H, s), 4.73 (2H, s), 7.04 (1H, d, J=1.2 Hz), 7.54 (1H, d, J=1.2 Hz), 7.76–7.94 (4H, m), 8.17 (1H, s). IR (KBr): 3193, 1667, 1003 cm$^{-1}$.

Example 3

Production of 2-ethyl-7-[1-hydroxy-1-(1H-imidazol-4-yl)-2-methylpropyl]-1,2-dihydro-3-benzo[e]isoindol-3-one

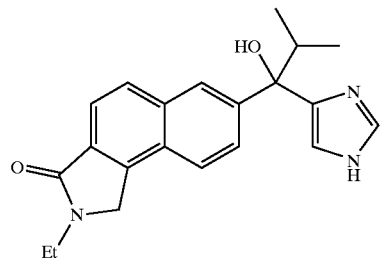

By a ring closure reaction, a detritylation reaction and purification in the same manner as in Example 1 using methyl 1-bromomethyl-6-[1-hydroxy-2-methyl-1-(1-trityl-1H-imidazol-4-yl)propyl]-2-naphthoate (1.52 g) and 70% aqueous ethylamine solution (3.0 ml), the title compound (0.63 g) was obtained as a colorless amorphous solid.

$^1$H-NMR (CDCl$_3$) δ: 0.80 (3H, d, J=6.6 Hz), 1.03 (3H, d, J=6.6 Hz), 1.30 (3H, t, J=7.2 Hz), 2.70 (1H, septet, J=6.6 Hz), 3.71 (2H, q, J=7.2 Hz), 4.60 (2H, s), 7.07 (1H, s), 7.56–7.79 (5H, m), 8.05 (1H, brs). IR (KBr): 1672, 1474, 1422, 826, 747 cm$^{-1}$.

Example 4

Production of 7-[1-hydroxy-1-(1H-imidazol-4-yl)-2-methylpropyl]-2-propyl-1,2-dihydro-3-benzo[e]isoindol-3-one

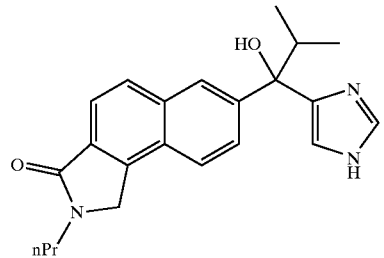

By a ring closure reaction, a detritylation reaction and purification in the same manner as in Example 1 using methyl 1-bromomethyl-6-[1-hydroxy-2-methyl-1-(1-trityl-1H-imidazol-4-yl)propyl]-2-naphthoate (1.32 g) and n-propylamine (2.5 ml), the title compound (0.59 g) was obtained as a colorless amorphous solid.

$^1$H-NMR (CDCl$_3$) δ: 0.80 (3H, d, J=6.6 Hz), 0.93–1.05 (6H, m), 1.74 (2H, sextet, J=7.4 Hz), 2.70 (1H, septet, J=6.6 Hz), 3.63 (2H, t, J=7.4 Hz), 4.62 (2H, s), 7.07 (1H, s), 7.57–7.80 (5H, m), 8.06 (1H, brs). IR (KBr): 1672, 1474, 1420, 826, 745 cm$^{-1}$.

Example 5

Production of 7-[1-hydroxy-1-(1H-imidazol-4-yl)-2-methylpropyl]-2-isopropyl-1,2-dihydro-3H-benzo[e]isoindol-3-one

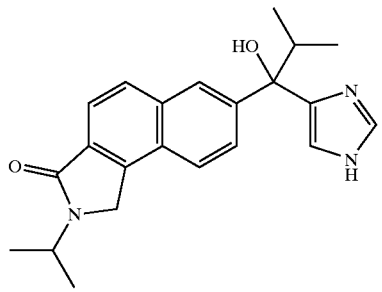

By a ring closure reaction, a detritylation reaction and purification in the same manner as in Example 1 using methyl 1-bromomethyl-6-[1-hydroxy-2-methyl-1-(1-trityl-1H-imidazol-4-yl)propyl]-2-naphthoate (1.32 g) and isopropylamine (3.0 ml), the title compound (0.56 g) was obtained as a colorless crystals.

$^1$H-NMR (CDCl$_3$) δ: 0.79 (3H, d, J=6.6 Hz), 1.03 (3H, d, J=6.6 Hz), 1.34 (6H, d, J=6.6 Hz), 2.70 (1H, septet, J=6.6 Hz), 3.50–4.00 (1H, br), 4.60 (2H, s), 4.69 (1H, septet, J=6.6 Hz), 7.06 (1H, s), 7.56–7.77 (5H, m), 8.06 (1H, s). IR (KBr): 1655, 1468, 1449, 1420, 1235, 824, 747 cm$^{-1}$.

Example 6

Production of 2-cyclopropyl-7-[1-hydroxy-1-(1H-imidazol-4-yl)-2-methylpropyl]-1,2-dihydro-3H-benzo[e]isoindol-3-one

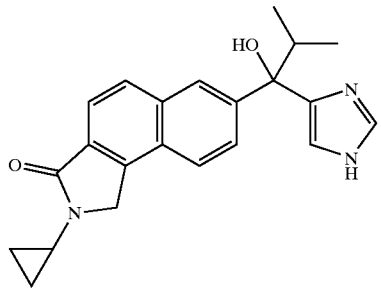

By a ring closure reaction, a detritylation reaction and purification in the same manner as in Example 1 using methyl 1-bromomethyl-6-[1-hydroxy-2-methyl-1-(1-trityl-1H-imidazol-4-yl)propyl]-2-naphthoate (1.32 g) and cyclopropylamine (3.0 ml), the title compound (0.58 g) was obtained as a colorless amorphous solid.

$^1$H-NMR (CDCl$_3$) δ: 0.80 (3H, d, J=6.6 Hz), 0.87–0.97 (4H, m), 1.03 (3H, d, J=6.6 Hz), 2.70 (1H, septet, J=6.6 Hz), 2.89–3.00 (1H, m), 3.50–4.00 (1H, br), 4.54 (2H, s), 7.07 (1H, s), 7.58–7.79 (5H, m), 8.05 (1H, brs). IR (KBr): 1673, 1468, 1451, 1420, 824, 745 cm$^{-1}$.

Example 7

Production of 7-[1-hydroxy-1-(1H-imidazol-4-yl)-2-methylpropyl]-2-(2,2,2-trifluoroethyl)-1,2-dihydro-3H-benzo[e]isoindol-3-one

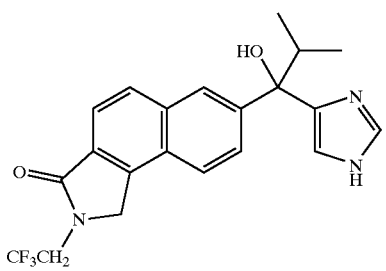

By a ring closure reaction, a detritylation reaction and purification in the same manner as in Example 1 using methyl 1-bromomethyl-6-[1-hydroxy-2-methyl-1-(1-trityl-1H-imidazol-4-yl)propyl]-2-naphthoate (0.66 g) and 2,2,2-trifluoroethylamine (2.0 ml), the title compound (0.34 g) was obtained as a colorless amorphous solid.

$^1$H-NMR (CDCl$_3$) δ: 0.80 (3H, d, J=6.6 Hz), 1.02 (3H, d, J=6.6 Hz), 2.76 (1H, septet, J=6.6 Hz), 3.30–3.70 (1H, br), 4.29 (2H, q, J=9.0 Hz), 4.83 (2H, s), 7.06 (1H, d, J=1.2 Hz), 7.58 (1H, d, J=1.2 Hz), 7.77–7.93 (4H, m), 8.21 (1H, s). IR (KBr): 1684, 1161, 1101, 826 cm$^{-1}$.

Example 8

Production of 2-(dimethylamino)-7-[1-hydroxy-1-(1H-imidazol-4-yl)-2-methylpropyl]-1,2-dihydro-3H-benzo[e]isoindol-3-one

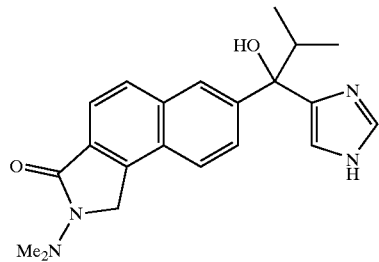

By a ring closure reaction, a detritylation reaction and purification in the same manner as in Example 1 using methyl 1-bromomethyl-6-[1-hydroxy-2-methyl-1-(1-H-imidazol-4-yl)propyl]-2-naphthoate (0.66 g) and 1,1-dimethylhydrazine (1.0 ml), the title compound (0.18 g) was obtained as a colorless amorphous solid.

$^1$H-NMR (CDCl$_3$+CD$_3$OD) δ: 0.78 (3H, d, J=6.6 Hz), 1.01 (3H, d, J=6.6 Hz), 2.72 (1H, septet, J=6.6 Hz), 3.20 (6H, s), 4.66 (2H, s), 7.04 (1H, d, J=1.0 Hz), 7.55–7.78 (4H, m), 7.91 (1H, d, J=8.4 Hz), 8.03 (1H, s). IR (KBr): 3220, 1537, 1424, 818 cm$^{-1}$.

Example 9

Production of 8-[1-hydroxy-1-(1H-imidazol-4-yl)-2-methylpropyl]-2,3-dihydrobenzo[f]phthalazin-4(1H)-one and 8-[1-hydroxy-1-(1H-imidazol-4-yl)-2-methylpropyl]benzo[f]phthalazin-4(3H)-one

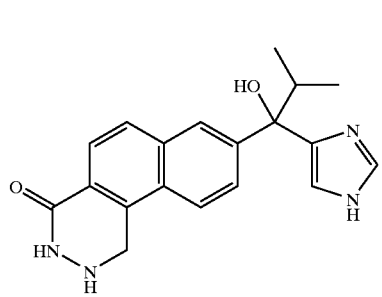

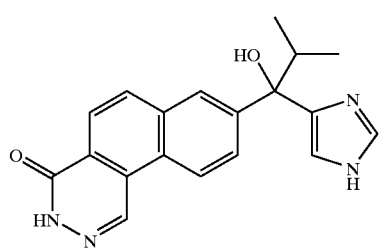

By a ring closure reaction, a detritylation reaction and purification in the same manner as in Example 1 using methyl 1-bromomethyl-6-[1-hydroxy-2-methyl-1-(1-trityl-1H-imidazol-4-yl)propyl]-2-naphthoate (0.62 g) and hydrazine monohydrate (0.35 ml), 8-[1-hydroxy-1-(1H-imidazol-4-yl)-2-methylpropyl]-2,3-dihydrobenzo[f]phthalazin-4(1H)-one (0.05 g) was obtained as a colorless amorphous solid and 8-[1-hydroxy-1-(1H-imidazol-4-yl)-2-methylpropyl]benzo[f]phthalazin-4(3H)-one (0.07 g) was obtained as colorless crystals.

8-[1-hydroxy-1-(1H-imidazol-4-yl)-2-methylpropyl]-2,3-dihydrobenzo[f]phthalazin-4(1H)-one $^1$H-NMR (CDCl$_3$+CD$_3$OD) δ: 0.79 (3H, d, J=6.6 Hz), 1.02 (3H, d, J=6.6 Hz), 2.72 (1H, septet, J=6.6 Hz), 4.56 (2H, s), 7.07 (1H, S), 7.55–7.74 (5H, m), 8.06 (1H, s). IR (KBr): 3194, 1682, 825, 743 cm$^{-1}$.

8-[1-hydroxy-1-(1H-imidazol-4-yl)-2-methylpropyl]benzo[f]phthalazin-4(3H)-one $^1$H-NMR (CDCl$_3$+CD$_3$OD) δ: 0.81 (3H, d, J=6.6 Hz), 1.04 (3H, d, J=6.6 Hz), 2.78 (1H, septet, J=6.6 Hz), 7.07 (1H, s), 7.58 (1H, s), 7.92 (1H, d, J=8.8 Hz), 8.10 (1H, d, J=8.8 Hz), 8.21 (1H, s), 8.23 (1H, d, J=8.8 Hz), 8.43 (1H, d, J=8.8 Hz), 8.92 (1H, s). IR (KBr): 3177, 1659 cm$^{-1}$.

Example 10

Production of 6-[1-hydroxy-1-(1H-imidazol-4-yl)-2-methylpropyl]-2,3-dihydro-1H-benzo[f]isoindol-1-one

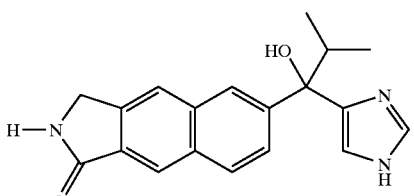

By a ring closure reaction, a detritylation reaction and purification in the same manner as in Example 1 using methyl 3-bromomethyl-6-[1-hydroxy-2-methyl-1-(1-trityl-1H-imidazol-4-yl)propyl]-2-naphthoate (5.00 g) and saturated ammonia methanol solution (30 ml), the title compound (1.46 g) was obtained as a colorless crystals.

$^1$H-NMR (CDCl$_3$+CD$_3$OD) δ: 0.80 (3H, d, J=7.0 Hz), 1.02 (3H, d, J=7.0 Hz), 2.76 (1H, septet, J=7.0 Hz), 4.56 (2H, s), 7.03 (1H, d, J=1.2 Hz), 7.53 (1H, d, J=1.2 Hz), 7.65 (1H, dd, J=8.4, 1.6 Hz), 7.90–7.96 (2H, m), 8.13 (1H, s), 8.31 (1H, s). IR (KBr): 3208, 1671 cm$^{-1}$.

Example 11

Production of 6-[1-hydroxy-1-(1H-imidazol-4-yl)-2-methylpropyl]-2-methyl-2,3-dihydro-1H-benzo[f]isoindol-1-one

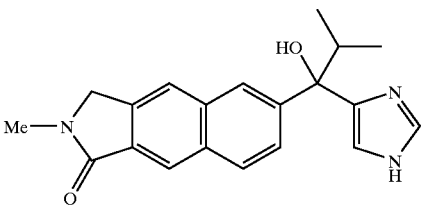

By a ring closure reaction, a detritylation reaction and purification in the same manner as in Example 1 using methyl 3-bromomethyl-6-[1-hydroxy-2-methyl-1-(1-trityl-1H-imidazol-4-yl)propyl]-2-naphthoate (0.99 g) and 40% methylamine methanol solution (8 ml), the title compound (0.11 g) was obtained as a colorless crystals.

$^1$H-NMR (CDCl$_3$+CD$_3$OD) δ: 0.81 (3H, d, J=6.6 Hz), 1.02 (3H, d, J=6.6 Hz), 2.70–2.90 (1H, m), 3.27 (3H, s), 4.59 (2H, s), 7.04 (1H, s), 7.54 (1H, s), 7.65–7.73 (1H, m), 7.92–7.96 (2H, m), 8.14 (1H, S), 8.27 (1H, S). IR (KBr): 3167, 1663, 1400, 1150, 810, 625 cm$^{-1}$.

Example 12

Production of 7-[1-hydroxy-1-(1H-imidazol-4-yl)-2-methylpropyl]-3,4-dihydrobenzo[g]phthalazin-1(2H)-one and 7-[1-hydroxy-1-(1H-imidazol-4-yl)-2-methylpropyl]benzo[g]phthalazin-1(2H)-one

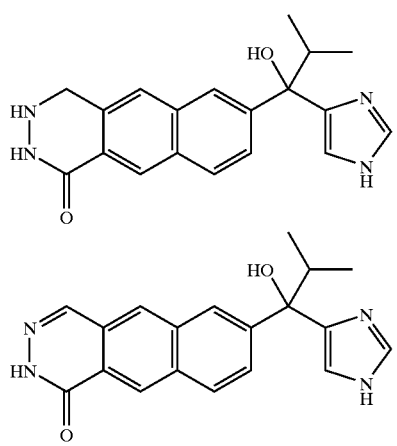

By a ring closure reaction, a detritylation reaction and purification in the same manner as in Example 1 using methyl 3-bromomethyl-6-[1-hydroxy-2-methyl-1-(1-trityl-1H-imidazol-4-yl)propyl]-2-naphthoate (0.95 g) and hydrazine monohydrate (0.50 ml), 7-[1-hydroxy-1-(1H-imidazol-4-yl)-2-methylpropyl]-3,4-dihydrobenzo[g]phthalazin-1(2H)-one (0.05 g) was obtained as a colorless amorphous solid and 7-[1-hydroxy-1-(1H-imidazol-4-yl)-2-methylpropyl]benzo[g]phthalazin-1(2H)-one (5 mg) was obtained as a colorless amorphous solid.

7-[1-hydroxy-1-(1H-imidazol-4-yl)-2-methylpropyl]-3,4-dihydrobenzo[g]phthalazin-1(2H)-one $^1$H-NMR (CDCl$_3$+CD$_3$OD) δ: 0.78 (3H, d, J=6.6 Hz), 1.01 (3H, d, J=6.6 Hz), 2.70 (1H, septet, J=6.6 Hz), 4.39 (1H, d, J=17.4 Hz), 4.40 (1H, d, J=17.4 Hz), 7.06 (1H, s), 7.53–7.58 (3H, m), 7.75 (1H, d, J=8.8 Hz), 8.01 (2H, s). IR (KBr): 3152, 1692, 1152, 808, 629 cm$^{-1}$.

7-[1-hydroxy-1-(1H-imidazol-4-yl)-2-methylpropyl]benzo[g]phthalazin-1(2H)-one $^1$H-NMR (CDCl$_3$+CD$_3$OD) δ: 0.81 (3H, d, J=7.0 Hz), 1.04 (3H, d, J=7.0 Hz), 2.77 (1H, septet, J=7.0 Hz), 7.08 (1H, s), 7.57 (1H, s), 7.77 (1H, d, J=8.8 Hz), 7.99 (1H, d, J=8.8 Hz), 8.17 (1H, s), 8.22 (1H, s), 8.29 (1H, s), 8.80 (1H, s). IR (KBr): 1655, 1346, 1096, 907, 814 cm$^{-1}$.

Example 13

Production of 7-[1-hydroxy-1-(1H-imidazol-4-yl)ethyl]-2-methyl-1,2-dihydro-3H-benzo[e]isoindol-3-one

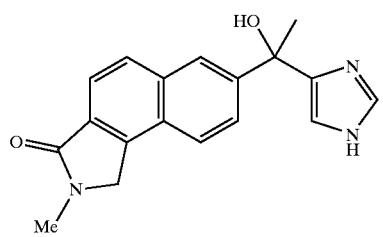

2-Methyl-7-[(1-trityl-1H-imidazol-4-yl)carbonyl]-1,2-dihydro-3H-benzo[e]isoindol-3-one (1.07 g) was dissolved in THF (22 mL) and cooled to 0° C., and then a solution (1.0 M: 3.0 mL) of methylmagnesium bromide in THF was added dropwise. The reaction mixture was stirred at room temperature for 1 hr. and a solution (1.0 M: 3.0 mL) of methylmagnesium bromide in THF was added. The mixture was further stirred at room temperature for 30 min., and 20% aqueous ammonium chloride solution was added to stop the reaction. The organic layer was separated, and the aqueous layer was extracted with ethyl acetate. The combined organic layers were washed with saturated brine, dried over anhydrous magnesium sulfate and concentrated. The residue was purified by column chromatography (carrier: silica gel, developing solvent: dichloromethane-methanol=100:1→40:1) to give 7-(1-hydroxy-1-(1-trityl-1H-imidazol-4-yl)ethyl]-2-methyl-1,2-dihydro-3H-benzo[e]isoindol-3-one (1.00 g) as an amorphous solid. This amorphous solid was dissolved in 90% formic acid (9 mL) and THF (9 mL) and the solution was stirred with heating at 60° C. for 2 hrs. The reaction mixture was concentrated and the residue was neutralized with saturated aqueous sodium hydrogen carbonate. Sodium chloride was added and the mixture was extracted three times with a mixed solution of ethyl acetate-THF (1:1) under salting out. The combined extracted layer was dried over anhydrous magnesium sulfate and concentrated. The residue was suspended in ethyl acetate, filtrated and recrystallized from ethanol-water to give the title compound (0.20 g) as pale-brown crystals.

$^1$H-NMR (CDCl$_3$+CD$_3$OD) δ: 1.97 (3H, s), 3.30 (3H, s), 4.75 (2H, s), 6.94 (1H, d, J=1.0 Hz), 7.58 (1H, d, J=1.0 Hz), 7.69 (1H, dd, J=8.8, 1.8 Hz), 7.77–7.93 (3H, m), 8.06 (1H, d, J=1.8 Hz). IR (KBr): 3180, 1671, 822, 743 cm$^{-1}$.

Example 14

Production of 7-[1-hydroxy-1-(1H-imidazol-4-yl)-3-methylbutyl]-2-methyl-1,2-dihydro-3H-benzo[e]isoindol-3-one

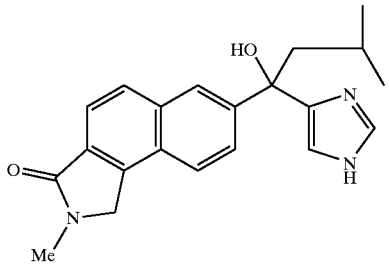

Using 2-methyl-7-[(1-trityl-1H-imidazol-4-yl)carbonyl]-1,2-dihydro-3H-benzo[e]isoindol-3-one (1.07 g) and isobutylmagnesium bromide, the same reaction and purification as in Example 13 were conducted. Then, a reaction using 90% formic acid was carried out in the same manner and a crude product was purified by column chromatography (carrier: silica gel, developing solvent: dichloromethane-methanol=40:1→10:1) to give the title compound (0.19 g) as a pale-brown amorphous solid.

$^1$H-NMR (CDCl$_3$) δ: 0.76 (3H, d, J=6.6 Hz), 0.95 (3H, d, J=6.6 Hz), 1.70–1.90 (1H, m), 2.24 (2H, d, J=5.8 Hz), 3.26 (3H, s), 4.61 (2H, s), 6.97 (1H, s), 7.60–7.79 (5H, m), 8.07 (1H, s). IR (KBr): 1674, 731 cm$^{-1}$.

Example 15

Production of 7-[1-hydroxy-2-methyl-1-(1-trityl-1H-imidazol-4-yl)propyl]-2-methyl-1,2-dihydro-3H-imidazol[e]isoindol-3-one

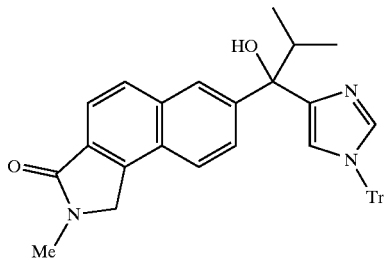

A solution (2 M: 79 mL) of 1-formyl-6-[1-hydroxy-2-methyl-1-(1-trityl-1H-imidazol-4-yl)propyl]-N,N-diisopropyl-2-naphthamide (35.0 g) and methylamine in THF was dissolved in dichloromethane (350 mL). Acetic acid (6.0 mL) was added dropwise to adjust the pH of the solution to 6–7. Sodium triacetoxyborohydride (33.5 g) was added to this solution, and the mixture was stirred at room temperature for 14 hrs. Saturated aqueous sodium hydrogen carbonate was added and the mixture was stirred for 30 min. and extracted with dichloromethane. The organic layer was washed with water and saturated brine and the solvent was evaporated under reduced pressure. Toluene was added to the residue and concentrated under reduced pressure to give a mixture containing 6-[1-hydroxy-2-methyl-1-(1-trityl-1H-imidazol-4-yl)propyl]-N,N-diisopropyl-1-(methylaminomethyl)-2-naphthamide as a colorless solid.

A solution (1.6 M: 115 mL) of butyllithium in hexane was added dropwise to a solution (500 mL) of diisopropylamine (25.8 mL) in THF at –70° C. After stirring the mixture at the same temperature for 10 min, a solution (150 mL) of a mixture containing 6-[1-hydroxy-2-methyl-1-(1-trityl-1H-imidazol-4-yl)propyl]-N,N-diisopropyl-1-(methylaminomethyl)-2-naphthamide in THF was added dropwise. After completion of the dropwise addition, the temperature of the reaction solution was slowly raised to –10° C. and the mixture was cooled to –50° C. Water was added to stop the reaction. The organic layer was separated and the aqueous layer was extracted with ethyl acetate. The combined organic layers were washed with saturated brine and the solvent was evaporated under reduced pressure. The residue was washed with isopropyl ether to give the title compound (28.8 g) as a colorless powder.

Example 16

Production of (–)-7-[1-hydroxy-1-(1H-imidazol-4-yl)-2-methylpropyl]-2-methyl-1,2-dihydro-3H-benzo[e]isoindol-3-one

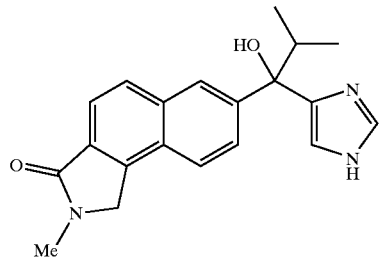

(–)-enantiomer

7-[1-Hydroxy-1-(1H-imidazol-4-yl)-2-methylpropyl]-2-methyl-1,2-dihydro-3H-benzo[e]isoindol-3-one was subjected to chromatography (eluent:hexane-ethanol=4:6) using an optical isomer separation column (CHIRALPAK AD, manufactured by Daicel Chemical Industries). As a first eluted fraction, (–)-7-[1-hydroxy-1-(1H-imidazol-4-yl)-2-methylpropyl]-2-methyl-1,2-dihydro-3H-benzo[e]isoindol-3-one was obtained.

optical purity >99% ee (CHIRALPAK AD) $[α]_D^{25}$ –31.2° (C=0.25, methanol)

Example 17

Production of 7-[1-(1-allyloxycarbonyl-1H-imidazol-4-yl)-1-hydroxy-2-methylpropyl]-2-methyl-1,2-dihydro-3H-benzo[e]isoindol-3-one

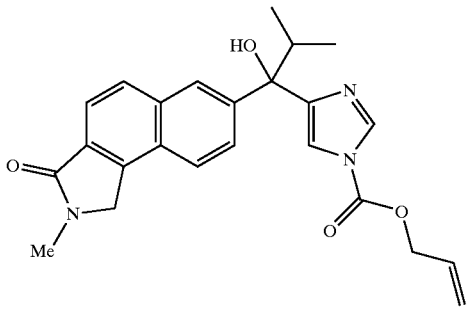

7-[1-Hydroxy-1-(1H-imidazol-4-yl)-2-methylpropyl]-2-methyl-1,2-dihydro-3H-benzo[e]isoindol-3-one (13.8 g) was suspended in DMF (400 ml) and the mixture was heated to 85° C. to give a homogeneous solution. This solution was cooled in an ice bath and triethylamine (8.6 ml) was added. Then allyloxycarbonyl chloride (5.2 ml) was slowly added and the reaction mixture was stirred at room temperature for 1.5 hrs. The reaction mixture was diluted with water and extracted twice with ethyl acetate. The extracted layers were combined, washed three times with water, dried over anhydrous magnesium sulfate and concentrated. The residue was purified by column chromatography (carrier: silica gel, developing solvent: dichloromethane-methanol= 100:1–40:1) to give the title compound (15.9 g) as colorless crystals.

$^1$H-NMR (CDCl$_3$) δ: 0.80 (3H, d, J=6.6 Hz), 1.01 (3H, d, J=6.6 Hz), 2.81 (1H, septet, J=6.6 Hz), 3.26 (3H, s), 3.41 (1H, s), 4.65 (2H, s), 4.86 (2H, d, J=6.2 Hz), 5.37 (1H, d, J=10.2 Hz), 5.44 (1H, d, J=16.8 Hz), 5.89–6.09 (1H, m), 7.46 (1H, s), 7.75–7.89 (4H, m), 8.09 (1H, s), 8.20 (1H, s). IR (KBr): 1761, 1682, 1400, 1265, 1013 cm$^{-1}$.

Example 18

Production of 7-[1-hydroxy-2-methyl-1-(1-trityl-1H-imidazol-4-yl)propyl]-2-methyl-1,2-dihydro-3H-benzo[e]isoindol-3-one

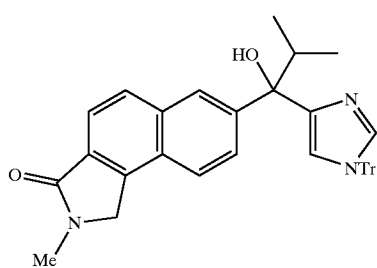

7-Bromo-2-methyl-1,2-dihydro-3H-benzo[e]isoindol-3-one (0.14 g) was suspended in THF (6 mL) and dissolved by heating. This solution was cooled to −70° C. and a solution (1.6 M: 0.75 mL) of n-butyllithium in hexane was slowly added dropwise. After stirring for 1 hr., a solution (1 mL) of 2-methyl-1-(1-trityl-1H-imidazol-4-yl)-1-propanone (0.16 g) in THF was added dropwise. After stirring at −70° C. for 30 min., 20% aqueous ammonium chloride was added to stop the reaction. The organic layer was separated, and the aqueous layer was extracted with ethyl acetate. The combined organic layers were washed with saturated brine, dried over anhydrous magnesium sulfate and concentrated. The residue was purified by column chromatography (carrier: silica gel, developing solvent: hexane-ethyl acetate, 1:1— ethyl acetate) to give the title compound (0.13 g) as colorless crystals.

$^1$H-NMR (CDCl$_3$) δ: 0.74 (3H, d, J=6.6 Hz), 0.97 (3H, d, J=6.6 Hz), 2.56 (1H, septet, J=6.6 Hz), 3.29 (3H, s), 3.69 (1H, br), 4.68 (2H, s), 6.83 (1H, d, J=1.4 Hz), 7.10–7.36 (16H, m), 7.76 (2H, s), 7.83 (2H, s), 8.11 (1H, s). IR (KBr): 3409, 1680, 704 cm$^{-1}$.

Example 19

Production of 7-[1-hydroxy-1-(1H-imidazol-4-yl) propyl]-2-methyl-1,2-dihydro-3H-benzo[e]isoindol-3-one (i) Production of 7-[1-hydroxy-1-(1-trityl-1H-imidazol-4-yl)propyl]-2-methyl-1,2-dihydro-3H-benzo[e]isoindol-3-one

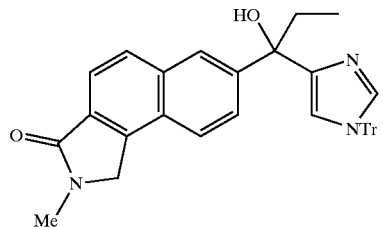

By the reaction in the same manner as in Example 18 using 7-bromo-2-methyl-1,2-dihydro-3H-benzo[e]isoindol-3-one (0.14 g) and 1-(1-trityl-1H-imidazol-4-yl)-1-propanone (0.17 g), the title compound (0.10 g) was obtained.

$^1$H-NMR (CDCl$_3$) δ: 0.84 (3H, t, J=7.2 Hz), 2.10–2.30 (2H, m), 3.26 (3H, s), 4.03 (1H, brs), 4.60 (2H, s), 6.83 (1H, s), 7.14–7.42 (16H, m), 7.56–7.81 (4H, m), 8.00 (1H, s). IR (KBr): 3350, 1682, 747, 702 cm$^{-1}$.

(ii) Production of 7-[1-hydroxy-1-(1H-imidazol-4-yl)propyl]-2-methyl-1,2-dihydro-3H-benzo[e]isoindol-3-one

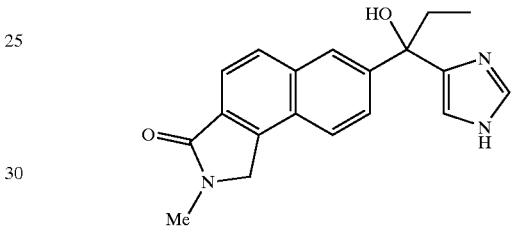

7-[1-hydroxy-1-(1-trityl-1H-imidazol-4-yl)propyl]-2-methyl-1,2-dihydro-3H-benzo[e]isoindol-3-one (100 mg) was dissolved in 90% formic acid (1 mL) and THF (1 mL) and the mixture was stirred with heating at 60° C. for 30 min. The reaction mixture was concentrated, and saturated aqueous sodium hydrogen carbonate was added to the residue. The mixture was extracted with a mixed solution of ethyl acetate-THF (1:1), dried and concentrated, and the residue was purified by silica gel chromatography to give the title compound (48 mg) as a colorless powder.

$^1$H-NMR (CDCl$_3$+CD$_3$OD) δ: 0.87 (3H, t, J=7.2 Hz), 2.16–2.44 (2H, m), 3.19 (3H, s), 4.50 (2H, s), 6.96 (1H, s), 7.52–7.72 (5H, m), 7.97 (1H, s). IR (KBr): 3200, 1674, 826, 747 cm$^{-1}$.

Experimental Example 1

Assay of Inhibitory Activity on Rat Steroid C$_{17,20}$-lyase

The activity was determined according to The Prostate, vol. 26, 140–150 (1995).

Testes were excised from 10- to 13-week-old male SD rats, homogenized, and centrifuged to give microsomes. [1,2-$^3$H]-17α-hydroxyprogesterone having a final concentration of 10 nM, NADPH solution and test compounds were dissolved in 10 μl of 100 mM phosphate buffer (pH 7.4) and microsome protein (7 μg/10 μl) was added. The reaction mixture was incubated at 37° C. for 7 minutes. Ethyl acetate (40 μl) was added and the mixture was centrifuged. The substrate and the products (androstenedione and testosterone) in the supernatant were separated by silica gel thin layer chromatography (TLC). The spots were detected and quantitatively determined by BAS 2000 Bioimage analyzer. The concentration of the test compounds necessary to reduce the amount of the products by 50% (IC$_{50}$) relative to the amount of the products without test compound (control) as 100% was calculated, and shown in Table 1.

TABLE 1

| Test compound | IC$_{50}$ (nM) |
|---|---|
| Example 1 | <10 |
| Example 2 | 15 |
| Example 3 | 23 |
| Example 10 | 42 |
| Example 14 | 22 |

Experimental Example 2

Assay of Inhibitory Activity on Testosterone Synthesis in Rats

Test compounds (25 mg/kg) were orally administered to 9-week-old male SD (Sprague Dawley) rats. Two hours after administration of the compounds, blood was drawn and testosterone concentration in the obtained serum was measured by radioimmunoassay. The percentage (T/C, %) of the testosterone concentration of test compounds administration group to that of the control group was calculated, and taken as the inhibitory activity on testosterone synthesis. The results are shown in Table 2.

TABLE 2

| Test compound | Testosterone synthesis inhibitory activity (T/C, %) |
|---|---|
| Example 1 | 6.0 |
| Example 16 (−)-enantiomer | 4.3 |

Experimental Example 3

Assay of Human CYP3A4-Inhibitory Activity

Performed as in the following according to Journal of Biological Chemistry, vol. 256, 11937 (1983).

A phosphate buffer solution (50 mM, pH 7.4) containing testosterone (final concentration 100 μM, hereinafter the same), human CYP3A4 (10 pmol/ml, manufactured by GENTEST), NADPH producing system (0.5 mM NADP, 5 mM glucose-6-phosphate, 5 mM magnesium chloride, 1.5 units/ml glucose-6-phosphate dehydrogenase) and the test compound was incubated at 37° C. for 30 min. Acetonitrile was added to the reaction mixture and the mixture was stirred and centrifuged. The 6β-hydroxytestosterone in the obtained supernatant was analyzed by high performance liquid chromatography. The concentration (IC$_{50}$) of the compound necessary for 50% inhibition was calculated taking the production amount without addition of the test compound as 100%. The results are shown in Table 3.

TABLE 3

| Test compound | IC$_{50}$ ($\mu$M) |
|---|---|
| Example 2 | >10 |
| Example 3 | >10 |
| Example 10 | >10 |

Formulation Example 1

Capsules

| | | |
|---|---|---|
| (1) | Compound obtained in Example 2 | 10 mg |
| (2) | lactose | 90 mg |
| (3) | microcrystalline cellulose | 70 mg |
| (4) | magnesium stearate | 10 mg |
| | One capsule | 180 mg |

The entire amount of the above (1), (2) and (3) and 5 mg of (4) were admixed. The mixture was granulated and the remaining 5 mg of (4) was added. The whole content was sealed in a gelation capsule.

Formulation Example 2

Tablets

| | | |
|---|---|---|
| (1) | Compound obtained in Example 1 | 10 mg |
| (2) | lactose | 35 mg |
| (3) | corn starch | 150 mg |
| (4) | microcrystalline cellulose | 30 mg |
| (5) | magnesium stearate | 5 mg |
| | One Tablet | 230 mg |

The entire amount of above (1), (2) and (3), 20 mg of (4) and 2.5 mg of (5) were admixed. The mixture was granulated and remaining 10 mg of (4) and 2.5 mg of (5) were added. The mixture was compression formed to give a tablet.

Industrial Applicability

The compound of the present invention and a salt thereof have a steroid $C_{17,20}$-lyase inhibitory activity and are useful for the prophylaxis or treatment of various diseases such as primary tumor, its metastasis and recurrence thereof, various symptoms that accompany these cancers, prostatic hypertrophy, virilism, hirsutism, male pattern alopecia, precocious puberty, endometriosis, uterus myoma, mastopathy, polycystic ovary syndrome and the like in mammal, which are affected by sex steroids and metabolites thereof.

This application is based on patent application Nos. 2000-353634 and 2000-382056 filed in Japan, the contents of which are hereby incorporated by reference.

What is claimed is:

1. A compound represented by the formula:

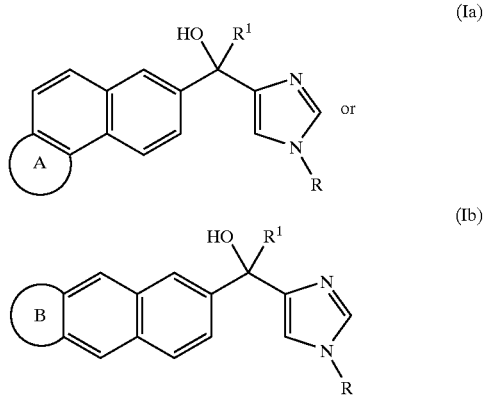

wherein R is (i) a hydrogen atom,
(ii) a formyl group or
(iii) a $C_{1-6}$ alkylcarbonyl group, a phenylcarbonyl group, a $C_{1-6}$ alkyl-oxycarbonyl group, a $C_{2-6}$ alkenyl-oxycarbonyl group, a phenyloxycarbonyl group, a $C_{7-10}$ aralkyloxy-carbonyl group, a trityl group, a phthaloyl group, or an N,N-dimethylaminomethylene group,
each of which optionally has 1 to 3 substituents selected from the group consisting of a halogen atom, a formyl, a $C_{1-6}$ alkyl-carbonyl and a nitro,
$R^1$ is a lower alkyl group or a cyclic alkyl group, and
ring A and ring B are each a 5-membered or 6-membered ring having an amide bond in the ring, optionally having a substituent selected from the group consisting of
(1) a $C_{1-10}$ linear or branched chain hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) an acylamino, (g) a carboxyl, (h) a $C_{1-10}$ alkoxycarbonyl, (i) an oxo, (j) a $C_{1-10}$ alkylcarbonyl, (k) a $C_{3-10}$ cycloalkyl, (l) a $C_{6-14}$ aryl, and (m) a 5 to 10-membered mono- to tri-cyclic aromatic heterocyclic group containing, besides the carbon atom, 1 or 2 kinds of hetero atoms selected from the group consisting of nitrogen, oxygen and sulfur,
(2) a $C_{3-18}$ cyclic hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) a $C_{1-10}$ alkylsulfonyl, (g) a mono- or di-$C_{1-4}$ alkylamino, (h) an acylamino, (i) a carboxyl, (j) a $C_{1-10}$ alkoxycarbonyl, (k) a $C_{3-10}$ alkynylcarbonyl, (l) a $C_{1-10}$ alkyl, (m) a $C_{3-10}$ cycloalkyl, (n) a $C_{6-14}$ aryl, and (o) a 5 to 10-membered mono- to tri-cyclic aromatic heterocyclic group containing, besides the carbon atom, 1 or 2 kinds of hetero atoms selected from the group consisting of nitrogen, oxygen and sulfur, (3) an amino group,
(4) a $C_{1-4}$ alkylamino group,
(5) a di-$C_{1-4}$ alkylamino group, and
(6) a $C_{1-4}$ alkanoylamino group, or a salt thereof.

2. The compound of claim 1, wherein the ring A and ring B are each represented by the formula:

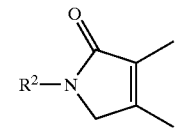

(IIa)

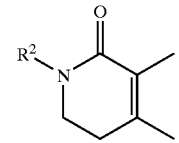

(IIb)

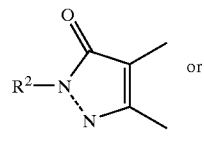

(IIc)

or

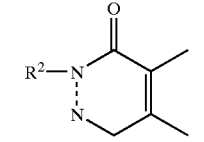

(IId)

wherein $R^2$ is
(1) a hydrogen atom,
(2) a $C_{1-10}$ linear or branched chain hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) an acylamino, a carboxyl, (h) a $C_{1-10}$ alkoxycarbonyl, (i) an oxo, (j) a $C_{1-10}$ alkylcarbonyl, (k) a $C_{3-10}$ cycloalkyl, (l) a $C_{6-14}$ aryl, and (m) a 5 to 10-membered mono- to tri-cyclic aromatic heterocyclic group containing, besides the carbon atom, 1 or 2 kinds of hetero atoms selected from the group consisting of nitrogen, oxygen and sulfur,
(3) a $C_{3-18}$ cyclic hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) a $C_{1-10}$ alkylsulfonyl, (g) a mono- or di-$C_{1-4}$ alkylamino, (h) an acylamino, (i) a carboxyl, (j) a $C_{1-10}$ alkoxycarbonyl, (k) a $C_{3-10}$ alkynylcarbonyl, (l) a $C_{1-10}$ alkyl, (m) a $C_{3-10}$ cycloalkyl, (n) a $C_{6-14}$ aryl, and (o) a 5 to 10-membered mono- to tri-cyclic aromatic heterocyclic group containing, besides the carbon atom, 1 or 2 kinds of hetero atoms selected from the group consisting of nitrogen, oxygen and sulfur,
(4) an amino group,
(5) a $C_{1-4}$ alkylamino group,
(6) a di-$C_{1-4}$ alkylamino group, or
(7) a $C_{1-4}$ alkanoylamino group, and
a dotted line indicates
a single bond or a double bond when $R^2$ is a hydrogen atom,
a single bond when $R^2$ is said $C_{1-10}$ linear or branched chain or $C_{3-18}$ cyclic hydrocarbon group or an amino group.

3. A compound represented by the formula:

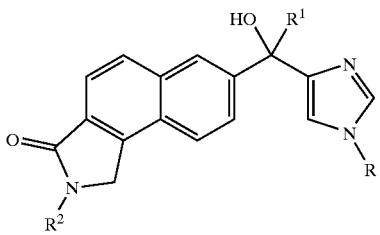

(III)

wherein R is (i) a hydrogen atom,
(ii) a formyl group or
(iii) a $C_{1-6}$ alkylcarbonyl group, a phenylcarbonyl group, a $C_{1-6}$ alkyl-oxycarbonyl group, a $C_{2-6}$ alkenyl-oxycarbonyl group, a phenyloxycarbonyl group, a $C_{7-10}$ aralkyloxy-carbonyl group, a trityl group, a phthaloyl group, or an N,N-dimethylaminomethylene group,
each of which optionally has 1 to 3 substituents selected from the group consisting of a halogen atom, a formyl, a $C_{1-6}$ alkyl-carbonyl and a nitro,
$R^1$ is a lower alkyl group or a cyclic alkyl group, and
$R^2$ is (1) a hydrogen atom,
(2) a $C_{1-10}$ linear or branched chain hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) an acylamino, (g) a carboxyl, (h) a $C_{1-10}$ alkoxycarbonyl, (i) an oxo, (j) a $C_{1-10}$ alkylcarbonyl, (k) a $C_{3-10}$ cycloalkyl, (l) a $C_{6-14}$ aryl, and (m) a 5 to 10-membered mono- to tri-cyclic aromatic heterocyclic group containing, besides the carbon atom, 1 or 2 kinds of hetero atoms selected from the group consisting of nitrogen, oxygen and sulfur,
(3) a $C_{3-18}$ cyclic hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) a $C_{1-10}$ alkylsulfonyl, (g) a mono- or di-$C_{1-4}$ alkylamino, (h) an acylamino, (i) a carboxyl, (j) a $C_{1-10}$ alkoxycarbonyl, (k) a $C_{3-10}$ alkynylcarbonyl, (l) a $C_{1-10}$ alkyl, (m) a $C_{3-10}$ cycloalkyl, (n) a $C_{6-14}$ aryl, and (o) a 5 to 10-membered mono- to tri-cyclic aromatic heterocyclic group containing, besides the carbon atom, 1 or 2 kinds of hetero atoms selected from the group consisting of nitrogen, oxygen and sulfur,
(4) an amino group,
(5) a $C_{1-4}$ alkylamino group,
(6) a di-$C_{1-4}$ alkylamino group, and
(7) a $C_{1-4}$ alkanoylamino group, or a salt thereof.

4. A pharmaceutical composition comprising a compound represented by the formula (Ia) or (Ib)

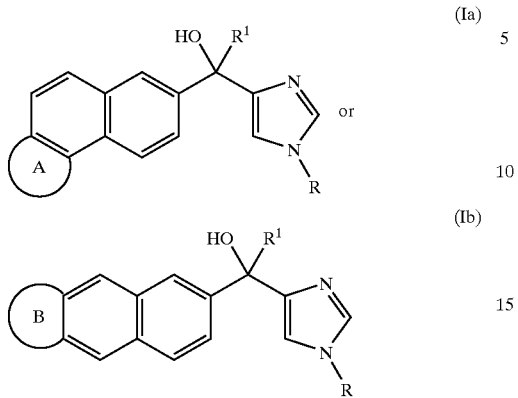

wherein R is (i) a hydrogen atom,
(ii) a formyl group or
(iii) a $C_{1-6}$ alkylcarbonyl group, a phenylcarbonyl group, a $C_{1-6}$ alkyl-oxycarbonyl group, a $C_{2-6}$ alkenyl-oxycarbonyl group, a phenyloxycarbonyl group, a $C_{7-10}$ aralkyloxy-carbonyl group, a trityl group, a phthaloyl group, or an N,N-dimethylaminomethylene group,
each of which optionally has 1 to 3 substituents selected from the group consisting of a halogen atom, a formyl, a $C_{1-6}$ alkyl-carbonyl and a nitro,
$R^1$ is a lower alkyl group or a cyclic alkyl group, and
ring A and ring B are each substituted a 5-membered or 6-membered ring having an amide bond in the ring, optionally having a substituent selected from the group consisting of
(1) a $C_{1-10}$ linear or branched chain hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) an acylamino, (g) a carboxyl, (h) a $C_{1-10}$ alkoxycarbonyl, (i) an oxo, (j) a $C_{1-10}$ alkylcarbonyl, (k) a $C_{3-10}$ cycloalkyl, (l) a $C_{6-14}$ aryl, and (m) a 5 to 10-membered mono- to tri-cyclic aromatic heterocyclic group containing, besides the carbon atom, 1 or 2 kinds of hetero atoms selected from the group consisting of nitrogen, oxygen and sulfur,
(2) a $C_{3-18}$ is cyclic hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (h) a $C_{1-10}$ alkylsulfonyl, (g) a mono- or di-$C_{1-4}$ alkylamino, (h) an acylamino, (i) a carboxyl, (j) a $C_{1-10}$ alkoxycarbonyl, (k) a $C_{3-10}$ alkynylcarbonyl, (l) a $C_{1-10}$ alkyl, (m) a $C_{3-10}$ cycloalkyl, (n) a $C_{6-14}$ aryl, and (o) a 5 to 10-membered mono- to tri-cyclic aromatic heterocyclic group containing, besides the carbon atom, 1 or 2 kinds of hetero atoms selected from the group consisting of nitrogen, oxygen and sulfur,
(3) an amino group,
(4) a $C_{1-4}$ alkylamino group,
(5) a di-$C_{1-4}$ alkylamino group, and
(6) a $C_{1-4}$ alkanoylamino group,
or a salt thereof.

5. A method for inhibiting a steroid $C_{17,20}$-lyase in a mammal in need thereof, which comprises administering an effective amount of a compound represented by the formula:

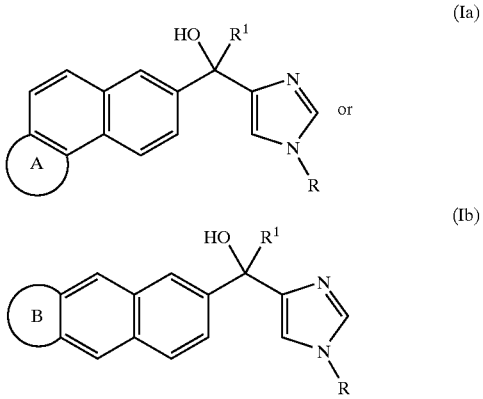

wherein R is (i) a hydrogen atom,
(ii) a formyl group or
(iii) a $C_{1-6}$ alkylcarbonyl group, a phenylcarbonyl group, a $C_{1-6}$ alkyl-oxycarbonyl group, a $C_{2-6}$ alkenyl-oxycarbonyl group, a phenyloxycarbonyl group, a $C_{7-10}$ aralkyloxy-carbonyl group, a trityl group, a phthaloyl group, or an N,N-dimethylaminomethylene group,
each of which optionally has 1 to 3 substituents selected from the group consisting of a halogen atom, a formyl, a $C_{1-6}$ alkyl-carbonyl and a nitro,
$R^1$ is a lower alkyl group or a cyclic alkyl group, and
ring A and ring B are each a 5-membered or 6-membered ring having an amide bond in the ring, optionally having a substituent selected from the group consisting of
(1) a $C_{1-10}$ linear or branched chain hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) an acylamino, (g) a carboxyl, (h) a $C_{1-10}$ alkoxycarbonyl, (i) an oxo, (i) a $C_{1-10}$ alkylcarbonyl, (k) a $C_{3-10}$ cycloalkyl, (l) a $C_{6-14}$ aryl, and (m) a 5 to 10-membered mono- to tri-cyclic aromatic heterocyclic group containing, besides the carbon atom, 1 or 2 kinds of hetero atoms selected from the group consisting of nitrogen, oxygen and sulfur,
(2) a $C_{3-18}$ cyclic hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) a $C_{1-10}$ alkylsulfonyl, (g) a mono- or di-$C_{1-4}$ alkylamino, (h) an acylamino, (i) a carboxyl, (j) a $C_{1-10}$ alkoxycarbonyl, (k) a $C_{3-10}$ alkynylcarbonyl, (l) a $C_{1-10}$ alkyl, (m) a $C_{3-10}$ cycloalkyl, (n) a $C_{6-14}$ aryl, and (o) a 5 to 10-membered mono- to tri-cyclic aromatic heterocyclic group containing, besides the carbon atom, 1 or 2 kinds of hetero atoms selected from the group consisting of nitrogen, oxygen and sulfur,
(3) an amino group,
(4) a $C_{1-4}$ alkylamino group,
(5) a di-$C_{1-4}$ alkylamino group, and
(6) a $C_{1-4}$ alkanoylamino group,
or a salt thereof,
to said mammal.

6. A method for treating an androgen- or estrogen-dependant tumor in a mammal in need thereof, which comprises administering an effective amount of a compound represented by the formula:

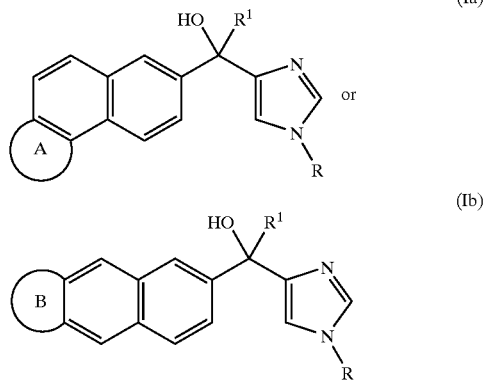

(Ia)

or (Ib)

wherein R is (i) a hydrogen atom,
(ii) a formyl group or
(iii) a $C_{1-6}$ alkylcarbonyl group, a phenylcarbonyl group, a $C_{1-6}$ alkyl-oxycarbonyl group, a $C_{2-6}$ alkenyl-oxycarbonyl group, a phenyloxycarbonyl group, a $C_{7-10}$ aralkyloxy-carbonyl group, a trityl group, a phthaloyl group, or an N,N-dimethylaminomethylene group,
  each of which optionally has 1 to 3 substituents selected from the group consisting of a halogen atom, a formyl, a $C_{1-6}$ alkyl-carbonyl and a nitro, $R^1$ is a lower alkyl group or a cyclic alkyl group, and ring A and ring B are each a 5-membered or 6-membered ring having an amide bond in the ring, optionally having a substituent selected from the group consisting of
(1) a $C_{1-10}$ linear or branched chain hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) an acylamino, (g) a carboxyl, (h) a $C_{1-10}$ alkoxycarbonyl, (i) an oxo, (j) a $C_{1-10}$ alkylcarbonyl, (k) a $C_{3-10}$ cycloalkyl, (l) a $C_{6-14}$ aryl, and (m) a 5 to 10-membered mono- to tri-cyclic aromatic heterocyclic group containing, besides the carbon atom, 1 or 2 kinds of hetero atoms selected from the group consisting of nitrogen, oxygen and sulfur,
(2) a $C_{3-18}$ cyclic hydrocarbon group optionally having 1 to 5 substituents selected from the group consisting of (a) a halogen atom, (b) a hydroxyl, (c) a alkoxy, (d) an acyloxy, (e) a $C_{1-10}$ alkylthio, (f) a $C_{1-10}$ alkylsulfonyl, (a) a mono- or di-$C_{1-4}$ alkylamino, (h) an acylamino, (i) a carboxyl, (j) a $C_{1-10}$ alkoxycarbonyl, (k) a $C_{3-10}$ alkynylcarbonyl, (l) a $C_{1-10}$ alkyl, (m) a $C_{3-10}$ cycloalkyl, (n) a $C_{6-14}$ aryl, and (o) a 5 to 10-membered mono- to tri-cyclic aromatic heterocyclic group containing, besides the carbon atom, 1 or 2 kinds of hetero atoms selected from the group consisting of nitrogen, oxygen and sulfur,
(3) an amino group,
(4) a $C_{1-4}$ alkylamino group,
(5) a di-$C_{1-4}$ alkylamino group, and
(6) a $C_{1-4}$ alkanoylamino group,
or a salt thereof,
to said mammal.

7. The method of claim 6, wherein said androgen- or estrogen-dependent tumor is uterine cancer or ovarian cancer.

8. The method of claim 6, wherein said androgen- or estrogen-dependant tumor is breast cancer or prostate cancer.

9. An androgen reducer comprising a compound represented by the formula (Ia) or (Ib)

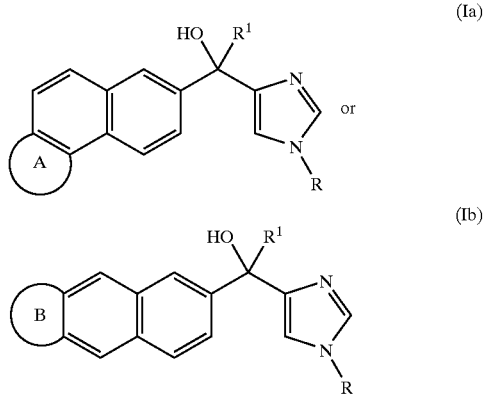

(Ia)

or (Ib)

wherein R is (i) a hydrogen atom,
(ii) a formyl group or
(iii) a $C_{1-6}$ alkylcarbonyl group, a phenylcarbonyl group, a $C_{1-6}$ alkyl-oxycarbonyl group, a $C_{2-6}$ alkenyl-oxycarbonyl group, a phenyloxycarbonyl group, a $C_{7-10}$ aralkyloxy-carbonyl group, a trityl group, a phthaloyl group, or an N,N-dimethylaminomethylene group,
  each of which optionally has 1 to 3 substituents selected from the group consisting of a halogen atom, a formyl, a $C_{1-6}$ alkyl-carbonyl and a nitro, $R^1$ is a lower alkyl group or a cyclic alkyl group, and ring A and ring B are each a 5-membered or 6-membered ring having an amide bond in the ring, optionally having a substituent selected from the group consisting of
(1) a $C_{1-10}$ linear or branched chain hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) an acylamino, (g) a carboxyl, (h) a $C_{1-10}$ alkoxycarbonyl, (i) an oxo, (j) a $C_{1-10}$ alkylcarbonyl, (k) a $C_{3-10}$ cycloalkyl, (l) a $_{6-14}$ aryl, and (m) a 5 to 10-membered mono- to tri-cyclic aromatic heterocyclic group containing, besides the carbon atom, 1 or 2 kinds of hetero atoms selected from the group consisting of nitrogen, oxygen and sulfur,
(2) a $C_{3-18}$ cyclic hydrocarbon group optionally having 1 to 5 substituents selected from the group consisting of (a) a halogen atom, (b) a hydroxyl, (c) a $C_{1-10}$ alkoxy, (d) an acyloxy, (e) a $C_{1-10}$ alkylthio, (f) a $C_{1-10}$ alkylsulfonyl, (g) a mono- or di-$C_{1-4}$ alkylamino, (h) an acylamino, (i) a carboxyl, (j) a $C_{1-10}$ alkoxycarbonyl, (k) a $C_{3-10}$ alkynylcarbonyl, (l) a $C_{1-10}$ alkyl, (m) a $C_{3-10}$ cycloalkyl, (n) a $C_{6-14}$ aryl, and (o) a 5 to 10-membered mono- to tri-cyclic aromatic heterocyclic group containing, besides the carbon atom, 1 or 2 kinds of hetero atoms selected from the group consisting of nitrogen, oxygen and sulfur,
(3) an amino group,
(4) a $C_{1-4}$ alkylamino group,
(5) a di-$C_{1-4}$ alkylamino group, and
(6) a $C_{1-4}$ alkanoylamino group,
or a salt thereof and
an LHRH modulator in combination.

10. A production method of a compound represented by the formula:

(VI)

wherein R is a hydrogen atom or a protecting group, and $R^1$ is a lower alkyl group or a cyclic alkyl group, or a salt thereof, which comprises reacting a compound represented by the formula:

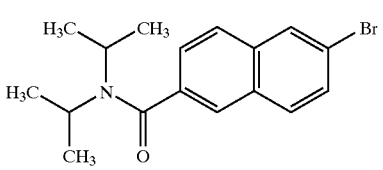

(IV)

with a compound represented by the formula:

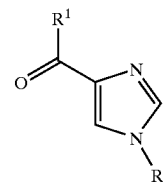

(V)

wherein each symbol is as defined above, or a salt thereof, in the presence of a base.

\* \* \* \* \*